(12) United States Patent
Igarashi et al.

(10) Patent No.: US 11,642,431 B2
(45) Date of Patent: May 9, 2023

(54) INFORMATION PROCESSING APPARATUS, CONTROL METHOD OF THE SAME, AND RECORDING MEDIUM

(71) Applicant: SONY CORPORATION, Tokyo (JP)

(72) Inventors: Go Igarashi, Tokyo (JP); Junya Suzuki, Kanagawa (JP); Shun Kaizu, Kanagawa (JP); Yusuke Otani, Kanagawa (JP); Yuto Ishizu, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 353 days.

(21) Appl. No.: 16/768,361

(22) PCT Filed: Sep. 7, 2018

(86) PCT No.: PCT/JP2018/033154
§ 371 (c)(1),
(2) Date: May 29, 2020

(87) PCT Pub. No.: WO2019/111471
PCT Pub. Date: Jun. 13, 2019

(65) Prior Publication Data
US 2020/0390926 A1 Dec. 17, 2020

(30) Foreign Application Priority Data
Dec. 8, 2017 (JP) .............................. JP2017-236404

(51) Int. Cl.
*A61L 9/12* (2006.01)
*A61B 5/00* (2006.01)
(Continued)

(52) U.S. Cl.
CPC .............. *A61L 9/12* (2013.01); *A61B 5/0022* (2013.01); *A61B 5/0024* (2013.01); *A61B 5/01* (2013.01);
(Continued)

(58) Field of Classification Search
CPC . A61L 9/01; A61L 9/12; A61B 5/0022; A61B 5/0024; A61B 5/01; A61B 5/16;
(Continued)

(56) References Cited

U.S. PATENT DOCUMENTS

2008/0062291 A1* 3/2008 Sako ....................... G06F 3/011
348/207.99
2009/0247883 A1 10/2009 Miyazaki et al.
(Continued)

FOREIGN PATENT DOCUMENTS

CA 2935160 A1 7/2015
CN 101551648 A 10/2009
(Continued)

OTHER PUBLICATIONS

International Search Report and Written Opinion of PCT Application No. PCT/JP2018/033154, dated Oct. 9, 2018, 10 pages of ISRWO.

*Primary Examiner* — Orlando Bousono
(74) *Attorney, Agent, or Firm* — Chip Law Group

(57) ABSTRACT

Provided is an information processing apparatus that is worn on a user's body for use. The information processing apparatus includes a sensor, a communication section, a control section, a power supply section, a housing section, a sticking section, and a sticking sensor. The control section controls the sensor and the communication section. The housing section accommodates the sensor, the communication section, the control section, and the power supply section. The sticking section fastens the housing section to the user. The sticking sensor detects a state of sticking between the user and the housing on the sticking section. The control section wirelessly sends a given signal to external equipment via the communication section in response to detection, by the sticking sensor, of the fact that the sticking section has (Continued)

peeled off from the user or is just about to peel off from the user.

19 Claims, 23 Drawing Sheets

(51) Int. Cl.
    *A61B 5/01*         (2006.01)
    *A61L 9/01*         (2006.01)

(52) U.S. Cl.
    CPC .......... *A61B 5/6813* (2013.01); *A61B 5/6833* (2013.01); *A61L 9/01* (2013.01)

(58) Field of Classification Search
    CPC ........ A61B 5/165; A61B 5/6801–6803; A61B 5/6813–6814; A61B 5/6821; A61B 5/683; A61B 5/6831–6839
    See application file for complete search history.

(56) References Cited

U.S. PATENT DOCUMENTS

| | | | |
|---|---|---|---|
| 2011/0022851 A1 | 1/2011 | Yokota et al. | |
| 2016/0287109 A1* | 10/2016 | Shim | H04N 21/42202 |
| 2016/0317088 A1 | 11/2016 | Fougere et al. | |
| 2017/0116492 A1* | 4/2017 | Bukshpan | A61B 5/4887 |
| 2017/0124272 A1* | 5/2017 | Reihman | G16H 40/67 |
| 2017/0124275 A1* | 5/2017 | Reihman | G16H 15/00 |
| 2017/0124350 A1* | 5/2017 | Reihman | A61B 5/746 |
| 2018/0110415 A1* | 4/2018 | Sasahara | A61B 5/0008 |
| 2018/0124548 A1* | 5/2018 | Tomiyasu | H04J 3/0602 |
| 2018/0217672 A1 | 8/2018 | Ito | |
| 2021/0216997 A1* | 7/2021 | Maragoudakis | H04W 12/065 |
| 2022/0148726 A1* | 5/2022 | Costantino | A61B 90/90 |

FOREIGN PATENT DOCUMENTS

| | | |
|---|---|---|
| CN | 101978649 A | 2/2011 |
| CN | 105939658 A | 9/2016 |
| CN | 108135567 A | 6/2018 |
| EP | 2244414 A1 | 10/2010 |
| EP | 3089662 A1 | 11/2016 |
| JP | 2000-121110 A | 4/2000 |
| JP | 2004-523289 A | 8/2004 |
| JP | 2006-345269 A | 12/2006 |
| JP | 2008-518709 A | 6/2008 |
| JP | 2009-240730 A | 10/2009 |
| JP | 2011-225521 A | 11/2011 |
| JP | 2014-106601 A | 6/2014 |
| JP | 2016-066188 A | 4/2016 |
| JP | 2017-500159 A | 1/2017 |
| KR | 10-2016-0105481 A | 9/2016 |
| RU | 2016131353 A | 2/2018 |
| WO | 2009/119079 A1 | 10/2009 |
| WO | 2015/103061 A1 | 7/2015 |
| WO | 2016/063587 A1 | 4/2016 |
| WO | 2017/018388 A1 | 2/2017 |
| WO | 2017/057015 A1 | 4/2017 |
| WO | 2017/068829 A1 | 4/2017 |

* cited by examiner

| | STICKING SENSOR | SOUND PICKUP SENSOR | SPEAKER | IMAGING ELEMENT | ODOR SENSOR | DISPLAY SECTION | ELECTROENCEPHALOGRAPHY SENSOR | ELECTRIC OUTPUT SECTION |
|---|---|---|---|---|---|---|---|---|
| TEMPLE | ○ | ○ | ○ | | | | ○ | △ |
| MIDDLE OF FOREHEAD/ UNDER EYE | ○ | | | ○ | | | | |
| BACK OF EAR | ○ | ○ | ○ | | | | ○ | △ |
| NECK | ○ | ○ | | | | | | |
| BASE OF NECK | ○ | ○ | ○ | | | | | |
| UPPER ARM/ FOREARM | ○ | | △ | | | ○ | | |
| WRIST | ○ | | △ | | | ○ | | |
| ABDOMEN /BACK | ○ | | | | ○ | | | ○ |

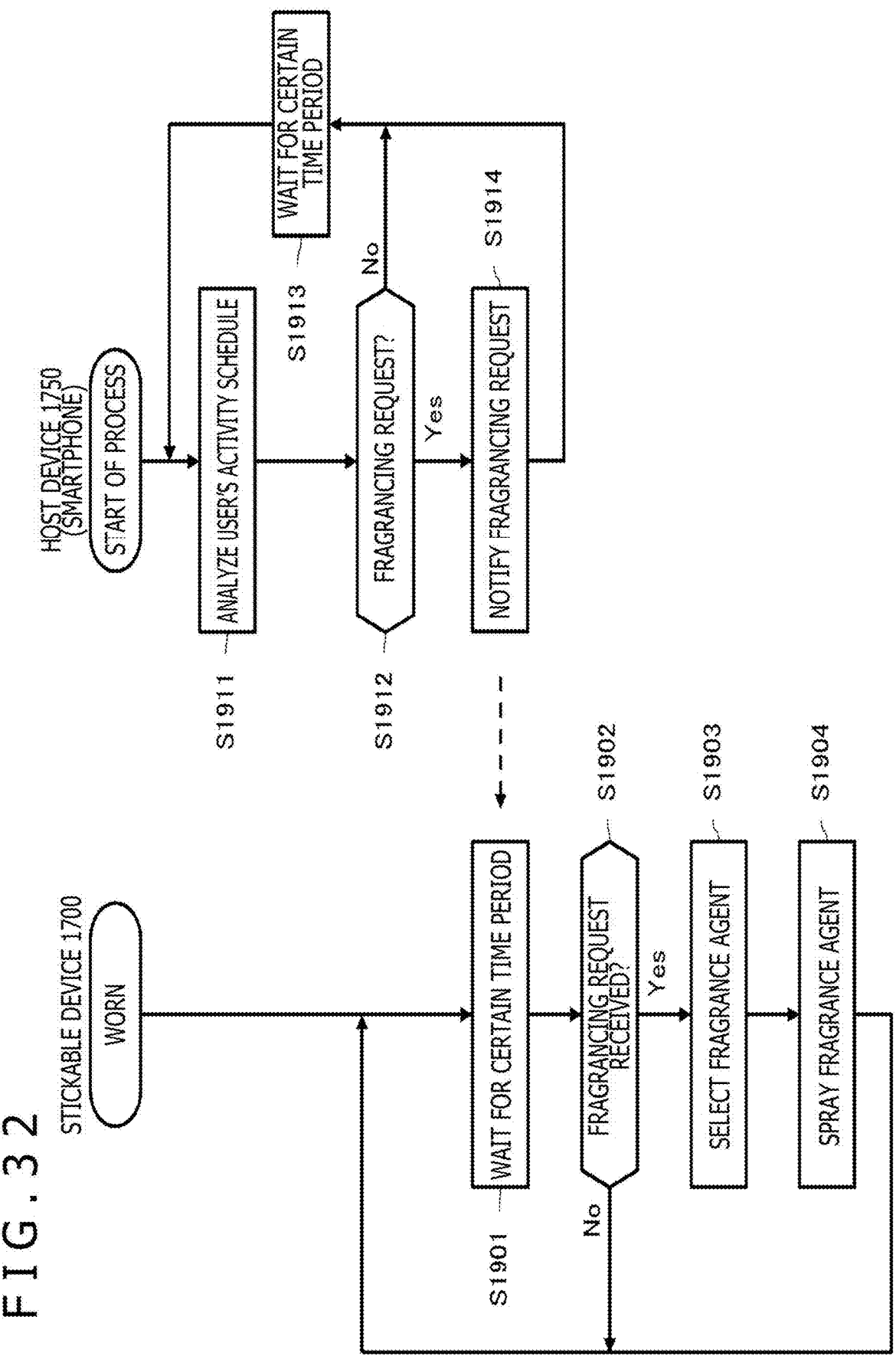

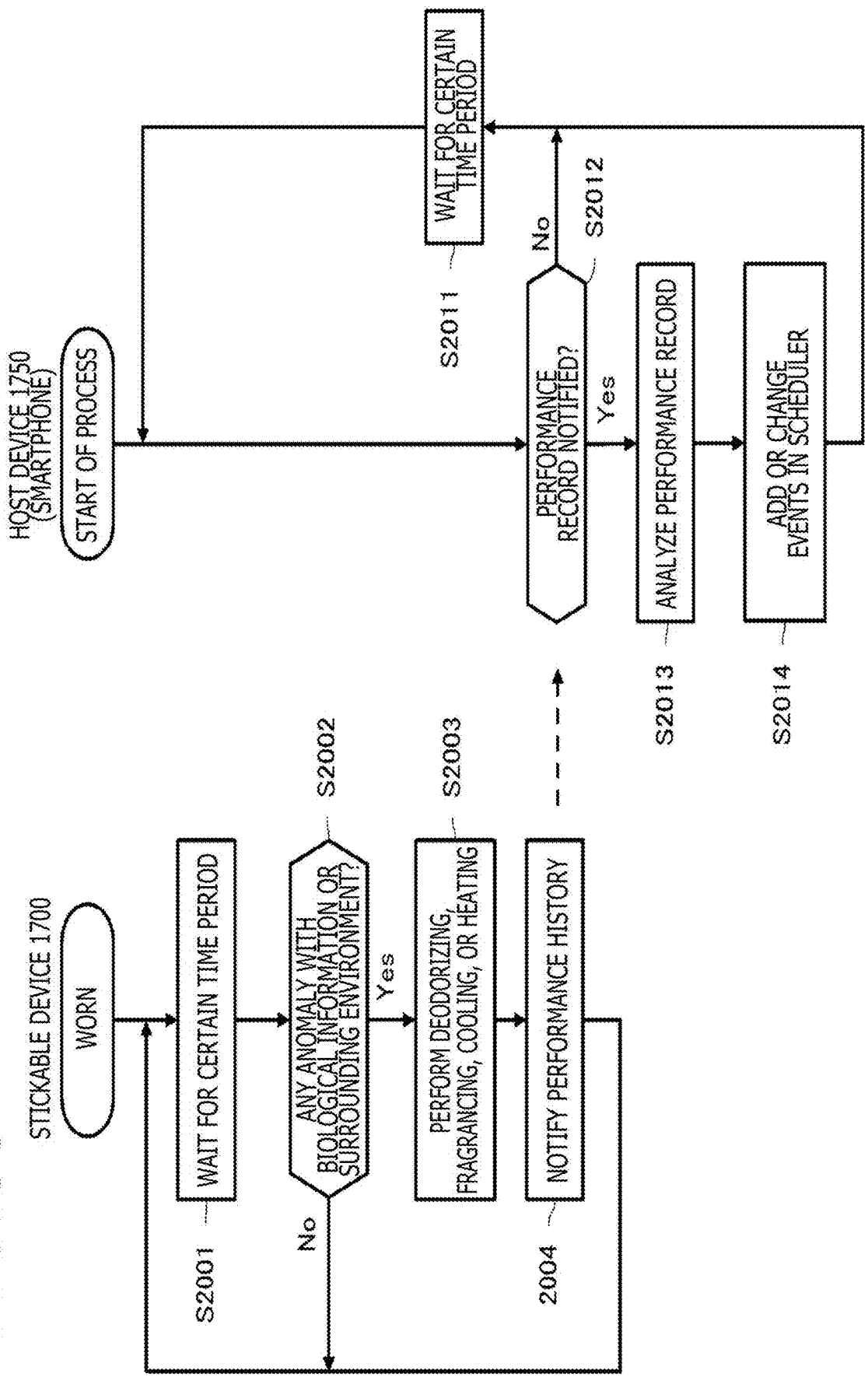

INFORMATION PROCESSING APPARATUS, CONTROL METHOD OF THE SAME, AND RECORDING MEDIUM

CROSS REFERENCE TO RELATED APPLICATIONS

This application is a U.S. National Phase of International Patent Application No. PCT/JP2018/033154 filed on Sep. 7, 2018, which claims priority benefit of Japanese Patent Application No. JP 2017-236404 filed in the Japan Patent Office on Dec. 8, 2017. Each of the above-referenced applications is hereby incorporated herein by reference in its entirety.

TECHNICAL FIELD

The technology disclosed in the present specification relates to an information processing apparatus worn on a user's body, a control method of the same, and a recording medium.

BACKGROUND ART

Recent years have seen growing use of wearable devices that are worn on various locations of users' bodies such as the arm and the head for use. Wearable devices are used, for example, to detect biological information, positional information, and other states of a user, keep track of records such as capturing images or recording sounds in the surroundings of the user, and present the user with a variety of types of information through sounds or the like. Wearable devices have found application in diverse fields such as those involving lifelog and supporting sports.

For example, a proposal has been made regarding a neckband type wearable device that is worn hanging from a user's neck in a wearing unit that goes half a lap around the user's neck from left and right sides to a rear side (back side) (refer, for example, to PTL 1).

CITATION LIST

Patent Literature

[PTL 1]
  WO2016/063587
[PTL 2]
  Japanese Patent Laid-Open No. 2006-345269
[PTL 3]
  Japanese Patent Laid-Open No. 2004-523289
[PTL 4]
  Japanese Patent Laid-Open No. 2008-518709
[PTL 5]
  Japanese Patent Laid-Open No. 2011-225521
[PTL 6]
  WO2017/068829

SUMMARY

Technical Problem

It is an object of the technology disclosed in the present specification to provide an information processing apparatus that is worn on a user's body for use, a control method thereof, and a recording medium.

Solution to Problem

A first aspect of the technology disclosed in the present specification is an information processing apparatus that includes a sensor, a communication section, a control section, a power supply section, a housing section, a sticking section, and a sticking sensor. The communication section wirelessly communicates with external equipment. The control section controls the sensor and the communication section. The power supply section supplies power to at least one of the sensor, the communication section, or the control section. The housing section accommodates at least one of the sensor, the communication section, the control section, or the power supply section. The sticking section fastens the housing section to a user. The sticking sensor detects a state of sticking between the user and the housing on the sticking section. The control section controls communication operation of the communication section in response to the sticking state detected by the sticking sensor.

The control section performs control such that a given signal is wirelessly sent to external equipment via the communication section in response to detection, by the sticking sensor, of the fact that the sticking section has peeled off from the user or is just about to peel off from the user.

Also, the information processing apparatus may further include a host device that engages in wireless communication via the communication section. The host device notifies the user in response to reception of the given signal. Also, the host device is capable of performing an authentication procedure of the user on the basis of sensor data detected by the sensor and cancels the user authentication established by the authentication procedure as a result of the reception of the given signal.

Also, the information processing apparatus further includes a storage section that stores internal information of the information processing apparatus. The storage section stores equipment information of the information processing apparatus, sensor data detected by the sensor, and so on. The control section initializes or deletes given information stored in the storage section in response to detection, by the sticking sensor, of the fact that the sticking section has peeled off from the user or is just about to peel off from the user.

Also, a surface of the sticking section is protected with release paper before use of the information processing apparatus. Then, the information processing apparatus is activated in response to peeling-off of the release paper from the sticking section. For example, the release paper includes a non-conductive section in the shape of a tongue piece that insulates the power supply section. Then, when the release paper is peeled off from the sticking section, the non-conductive section is detached, bringing the power supply section into a conductive state and initiating the activation of the information processing apparatus. Alternatively, the control section activates the information processing apparatus in response to the detection, by the sticking sensor, of the fact that the release paper has been peeled off from the sticking section.

Also, a second aspect of the technology disclosed in the present specification is an information processing method of an information processing apparatus that includes a sensor, a communication section, a control section, a power supply section, a housing section, a sticking section, and a sticking sensor. The communication section wirelessly communicates with external equipment. The control section controls the sensor and the communication section. The power supply section supplies power to at least one of the sensor, the communication section, or the control section. The housing section accommodates at least one of the sensor, the communication section, the control section, or the power supply section. The sticking section fastens the housing section to the user. The sticking sensor detects a state of sticking between the user and the housing on the sticking section. The control method includes a step of acquiring detection results of the sticking sensor, a step of determining whether the sticking section has peeled off from the user or is just about to peel off from the user on the basis of the detection results, and a step of wirelessly sending a given signal to external equipment via the communication section when the sticking section has peeled off from the user or is just about to peel off from the user.

Also, a third aspect of the technology disclosed in the present specification is a recording medium recording a computer program for controlling an information processing apparatus that includes a sensor, a communication section, a control section, a power supply section, a housing section, a sticking section, and a sticking sensor. The communication section wirelessly communicates with external equipment. The control section controls the sensor and the communication section. The power supply section supplies power to at least one of the sensor, the communication section, or the control section. The housing section accommodates at least one of the sensor, the communication section, the control section, or the power supply section. The sticking section fastens the housing section to the user. The sticking sensor detects a state of sticking between the user and the housing on the sticking section. The computer program is written in a computer-readable form to cause a computer to perform a step of acquiring detection results of the sticking sensor, a step of determining whether the sticking section has peeled off from the user or is just about to peel off from the user on the basis of the detection results, and a step of wirelessly sending a given signal to external equipment via the communication section when the sticking section has peeled off from the user or is just about to peel off from the user.

Advantageous Effect of Invention

The technology disclosed in the present specification can provide an information processing apparatus that is worn on a user's body for use, a control method thereof, and a recording medium.

It should be noted that the effects recited in the present specification are merely illustrative and do not limit the effects of the present invention. Also, the present invention may bring about additional effects other than the above effects.

Still other objects, features, and advantages of the technology disclosed in the present specification will become apparent from more detailed description based on an embodiment and attached drawings which will be described later.

BRIEF DESCRIPTION OF DRAWINGS

FIG. 32 is a flowchart illustrating a processing sequence for the host device 1750 to carry out fragrance control on the side of the stickable device 1700 on the basis of a user's activity schedule.

FIG. 33 is a flowchart illustrating a processing sequence for the host device 1750 to adjust a schedule for making a fragrancing request on the basis of a history of performing fragrancing on the side of the stickable device 1700.

DESCRIPTION OF EMBODIMENT

Figure 1:
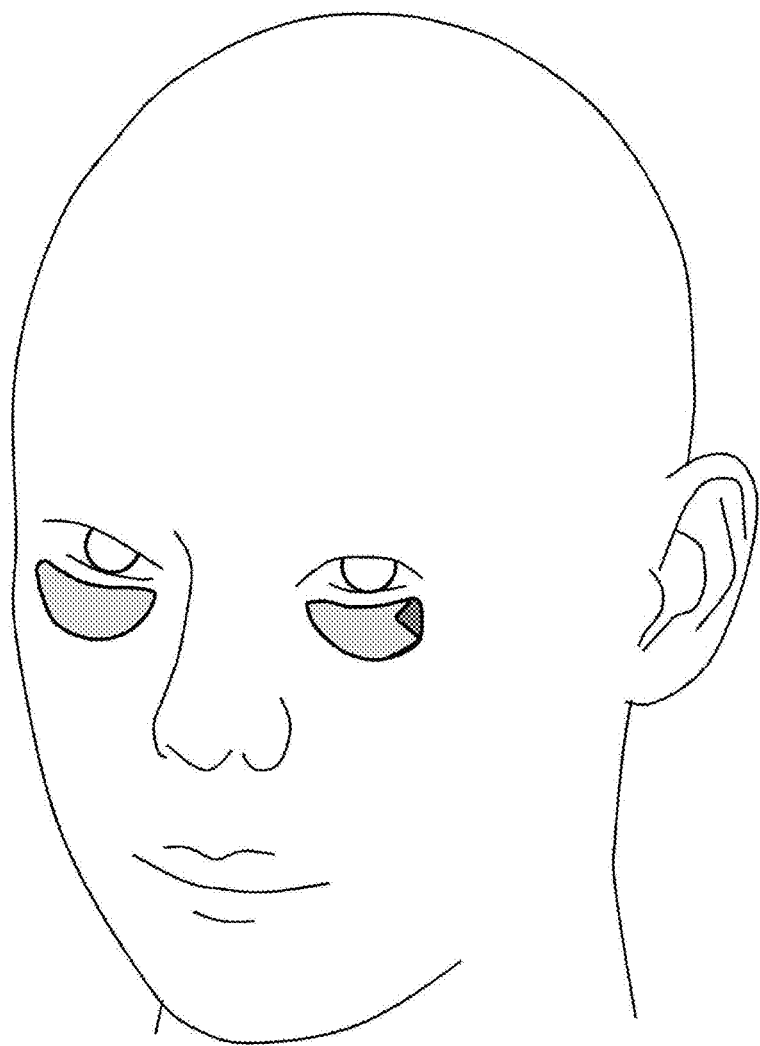
FIG. 1 is an exemplary diagram illustrating a manner in which a stickable device stuck under a user's eye is about to peel off.

A detailed description will be given below of an embodiment of the technology disclosed in the present specification with reference to drawings.

Wearable devices such as a watch-type information terminal and an eyeglass-type information terminal worn on the arm, the head, or other locations are well known. For example, a watch-type information terminal is wrapped around a user's wrist or its nearby location for use similarly to a wristwatch, and provides not only basic functions of a watch but also a number of functions including email and other text communication, activity amount measurement and measurement result display such as a pedometer, and music reproduction. Also, an eyeglass-type information terminal allows the user wearing the information terminal to receive information such as navigation and latest news at all times by presenting information in part of the user's field of view.

Many conventional wearable devices are apparently noticeable when worn by users. For example, eyeglass-type information terminals differ significantly in shape from ordinary vision correction eyeglasses. This may give a sense of discomfort to surrounding people, raising a concern that widespread use of wearable devices may be hindered. A possible approach would be to introduce new ideas to main body designs of wearable devices to ensure that the user himself or herself and surrounding people can be receptive to the wearable devices. Also, it is not easy to eliminate a user's phycological sense of discomfort toward the use of an apparatus in a new form.

For this reason, the present specification proposes the following regarding a stickable information processing apparatus (also referred to as a "stickable device") that is directly stuck to the user's body surface (or skin) for use. The information processing apparatus stuck to the user's body surface causes only minimal appearance change, thus giving no sense of discomfort to surrounding people. Also, this type of information processing apparatus is casual and comfortable to wear for the user himself or herself and does not make the user perceive a sense of wearing the apparatus to the extent possible. That is, the user wearing a stickable information processing apparatus does not perceive the presence thereof, and the stickable information processing apparatus is not noticed by surrounding people. However, when the user uses it, the stickable information processing apparatus is reliably functional, giving a casual and comfortable sense of use.

The stickable information processing apparatus proposed in the present specification is basically configured as a physically single apparatus and stuck to one of the locations of the user's body described above for use. As a modification, the information processing apparatus is configured as a set of two or more divided apparatuses which are physically separated from each other and stuck to two or more of the locations described above. In the latter case, the individual divided apparatuses are configured in such a manner as to be connected to each other by using wireless communication, biometric communication, or the like and coordinate with each other to function as a single information processing apparatus.

The stickable information processing apparatus proposed in the present specification includes, as its basic components, a sensor, a communication section, a control section, a power supply section, a housing section, a sticking section, and a sticking sensor. The communication section wirelessly communicates with external equipment. The control section controls the sensor and the communication section. The power supply section supplies power to at least one of the sensor, the communication section, or the control section. The housing section accommodates at least one of the sensor, the communication section, the control section, or the power supply section. The sticking section fastens the housing section to the user. The sticking sensor detects a state of sticking between the user and the housing on the sticking section. The sensor described above includes one or more sensor elements. Also, the stickable information processing apparatus wirelessly sends, as its basic operation, sensor data detected by the sensor to external equipment via the communication section.

Also, as characteristic operation of the stickable information processing apparatus proposed in the present specification, the control section controls communication operation of the communication section in response to the sticking state between the sticking section and the user detected by the sticking sensor. Specifically, the control section performs control such that a given signal is wirelessly sent to external equipment via the communication section in response to the detection, by the sticking sensor, of the fact that the sticking section has begun to peel off from the user or is just about to peel off from the user. FIG. 1 illustrates that, of the information processing apparatuses stuck under the user's left and right eyes, the one on the left has begun to peel off.

Also, the information processing apparatus may include a host device that wirelessly communicates via the communication section. The host device may have a function to notify, to the user, information including, for example, the fact that the sticking section has begun to peel off from the user or is just about to peel off from the user in response to reception of a given signal. Also, the host device may further have a function to receive sensor data of the sensor through wireless communication and perform a user authentication procedure on the basis of the sensor data. Then, the host device may cancel the user authentication established by the authentication procedure as a result of the reception of the given signal.

The stickable information processing apparatus may include, as one of the sensors described above, a sound pickup sensor that has a sound pickup function, and may wirelessly send audio data detected by the sound pickup sensor to external equipment by using the communication section. IoT (Internet of Things) devices do not have conventional input devices such as a mouse or a keyboard, and user interfaces (UIs) using sound information are more promising than those using text information. Therefore, a sound pickup sensor can be considered an essential component of the information processing apparatus. The sound pickup sensor includes, for example, a compact microphone and other components.

The main body of the stickable information processing apparatus can be stuck, for use, near the eyeball such as under the eye, to a user's head or face portion such as the temple, back of the ear, under the chin, the neck, the base of the neck, or the throat, or to a user's torso or limb portion such as the back, the upper arm, the forearm, the wrist, back of the hand, the neck, base of the neck, or the throat. In the case where the main body of the stickable information processing apparatus is stuck near user's vocal cords for use, it is possible to effectively pick up user's real voice through air conduction from the mouth and flesh conduction or bone conduction in the head. This makes it easier for the information processing apparatus to provide a sound sensing function for lifelog. Also, when stuck to a location such as under the chin, the information processing apparatus is inconspicuous and does not give a sense of discomfort to surrounding people.

A. System Configuration

Figure 2:
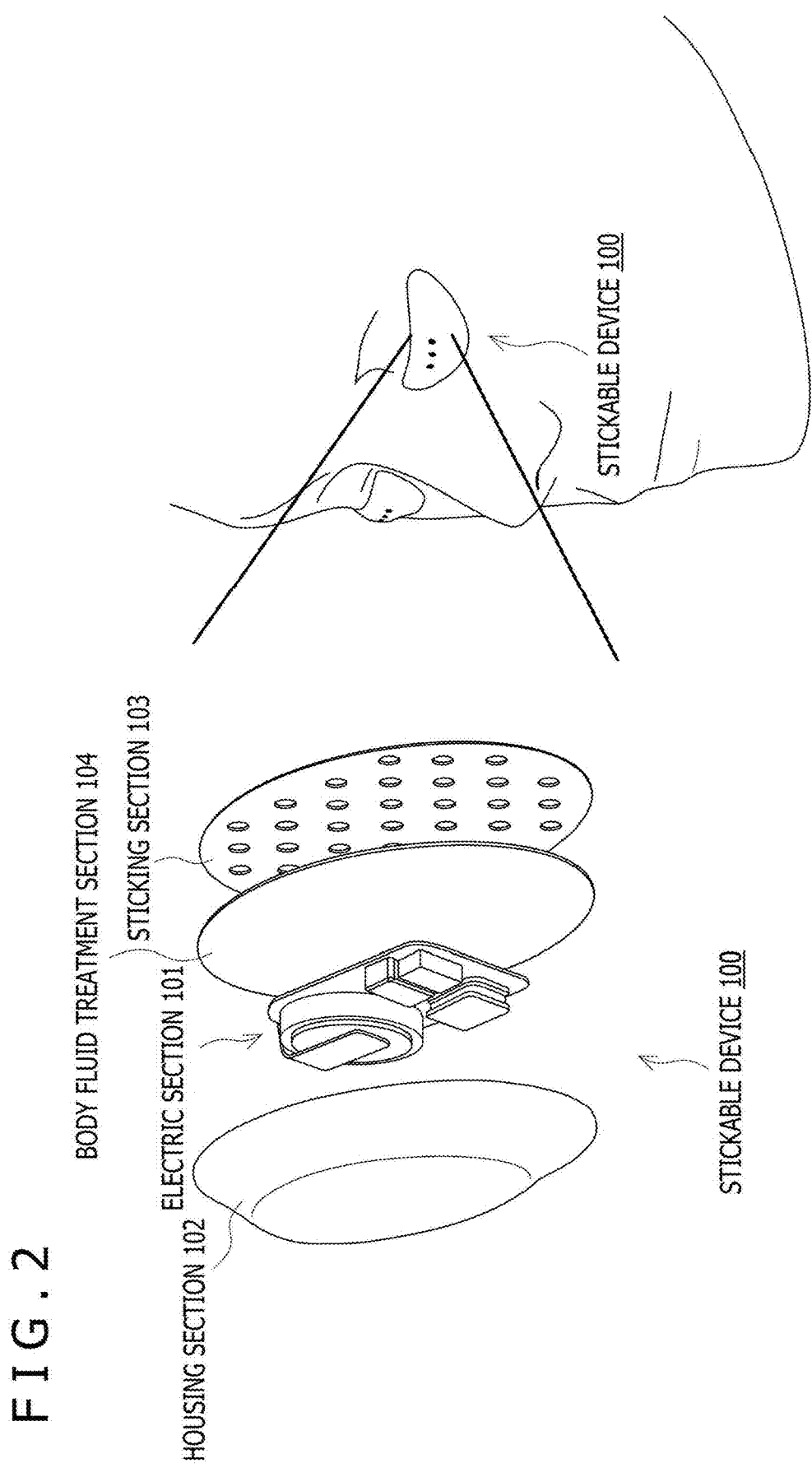
FIG. 2 is a diagram illustrating a manner in which a stickable device 100 is stuck under the user's eye and an exploded view of the stickable device 100.
Figure 3:
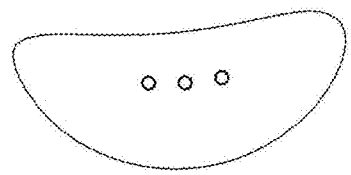
FIG. 3 is a front view of the stickable device 100 illustrated in FIG. 2.
Figure 4:
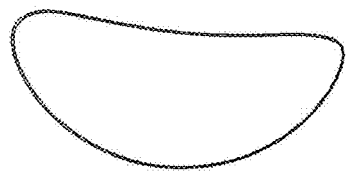
FIG. 4 is a rear view of the stickable device 100 illustrated in FIG. 2.
Figure 5:
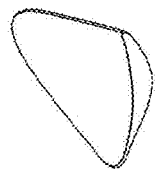
FIG. 5 is a right-side view of the stickable device 100 illustrated in FIG. 2.
Figure 6:
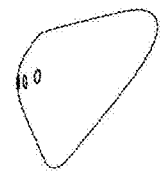
FIG. 6 is a left-side view of the stickable device 100 illustrated in FIG. 2.
Figure 7:
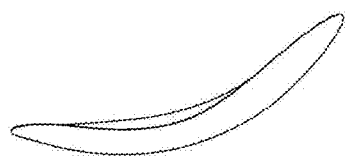
FIG. 7 is a top view of the stickable device 100 illustrated in FIG. 1.
Figure 8:
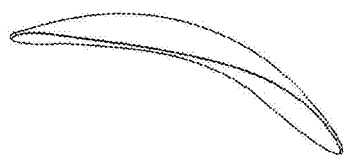
FIG. 8 is a bottom view of the stickable device 100 illustrated in FIG. 1.

FIG. 2 illustrates a manner in which a stickable device 100 is stuck under the user's left eye and an exploded view of the stickable device 100, as one example. Also, FIGS. 3 to 8 illustrate a front view, a rear view, a right-side view, a left-side view, a top view, and a bottom view of the stickable device 100 stuck under the user's eye, respectively.

The stickable device 100 includes an electric section 101, a housing section 102, and a sticking section 103. The electric section 101 includes a substrate having an imaging sensor or other types of sensor and circuit components such as the communication section, the control section, and the power supply section. The housing section 102 accommodates the electric section 101. The sticking section 103 fastens the housing section 102 to the user's body by sticking the housing section 102 to the user's body surface. Also, the stickable device 100 illustrated has a body fluid treatment section 104 stacked on top of the sticking section 103.

The housing section 102 should preferably be a flexible soft shell in consideration of preventing damage caused when the housing section 102 comes in contact with a location of the user's body other than that where the main body of the stickable device 100 is stuck or with the body of a surrounding individual. Also, although the housing section 102 includes a metallic or non-metallic raw material, the housing section 102 accommodates a communication section. Therefore, it is necessary for the housing section 102 to be transmissive to radio waves. As is clear from FIGS. 2 and 3, of an outline of the housing section 102 (or the main body of the stickable device 100), the upper shape includes a curve running along the shape of the lower half of the eye (shape on the lower eyelash side), thus giving no sense of discomfort in terms of appearance. Also, when stuck to the user's body (e.g., face), the stickable device 100 does not have a good fit if the outline thereof has edges. Therefore, the outline thereof includes a curve. Also, at least one opening portion is formed on the surface of the housing section 102 (in other words, on the front surface of the main body of the stickable device 100). Each opening portion has a transparent cover to protect the imaging section (transparent cover in the case of a lensless camera) or an imaging lens.

Also, the surface (or appearance surface) of the housing section 102 should preferably be adjusted to have a flesh color to ensure that the location to which the main body of the stickable device 100 is stuck develops only a minimal change in appearance. Alternatively, the surface of the housing section 102 may have a transparent color or may be painted in a fashionable color. Also, the housing section 102 may be adjusted in color or an uneven shape may be formed thereon to resemble stains or projections and depressions of the skin in the location to which the stickable device 100 is stuck. Also, for example, a pattern of a tattoo sticker may be formed on the surface of the housing section 102 to represent the user's personality.

It should be noted, however, that the main body of the stickable device 100 is assumably stuck not only under the user's eye but also to various other locations on the surface of the user's body. For this reason, the housing section 102 or the main body of the stickable device 100 may have a different outer shape from one location to which it is stuck to another. Alternatively, the housing section 102 or the main body of the stickable device 100 may have the same outer shape in all locations to which it is stuck.

Also, the housing section 102 should preferably be water-repellent by including a water-repellent material, providing water-repellent coating on the surface thereof, or the like. If the surface of the housing section 102 is not water-repellent, a body fluid (e.g., sweat) secreted or discharged from the user's skin, rain or the like penetrates into the housing section 102, possibly damaging the circuit components included in the electric section 101 and deteriorating adhesiveness of the sticking section 103 that lies further below the electric section 101.

The electric section 101 includes a substrate having one or more sensors, the communication section, the control section, the power supply section and the like, and circuit components thereof (described earlier). The control section includes, for example, a processor and a memory and controls processing of sensor data detected by the sensor, wireless signal transmission and reception procedures performed by the communication section, and the like. Also, the memory stores equipment information of the stickable device 100, sensor data detected by the sensor, and so on.

The substrate included in the electric section 101 should preferably be flexible and expandable so as to follow the change in the user's body surface (free-form surface) to which the main body of the stickable device 100 is stuck. For example, the flexibility and expandability are improved by using a flexible substrate and forming cuts in the flexible substrate in two or more axial directions, thus making it easier to follow the free-form surface. Conversely, if the substrate is not flexible or expandable, the main body of the stickable device 100 is more likely to peel off from the user's body surface to which it has been stuck.

The sticking section 103 is in the form of a sheet and has a stickable adhesive surface, making it possible to fasten the main body of the stickable device 100 to the user's body by sticking the sticking section 103 to the user's body surface. Also, the sticking section 103 should preferably be permeable to moisture (or permeable to water or liquid) in consideration of secretion or discharge of considerable amounts of body fluids (e.g., sweat) from the user's skin. For example, the sticking section 103 includes a porous material having one or more openings.

The adhesive surface of the sticking section 103 should preferably include an adhesive agent that is applicable on skin (e.g., does not irritate skin and unlikely to cause allergies). Also, when unused, the adhesive surface of the sticking section 103 should preferably be protected with release paper (not illustrated) to prevent dust from adhering to the adhesive surface and maintain a sticking capability. In addition, the stickable device 100 may be put into an in-use state when the release paper is peeled off from the sticking section 103, turning on the power for the stickable device 100.

The body fluid treatment section 104 treats the user's body fluids that penetrate via the openings on the sticking section 103, thus blocking the body fluids from reaching the electric section 101. The body fluid treatment section 104 includes, for example, a meshed material such as macromolecular polymer moisture absorbent. The body fluid treatment section 104 guides the body fluids through capillary phenomenon and discharges them into the environment (out of the stickable device 100). The body fluid treatment section 104 should preferably be configured as a spare part.

When equipped with an imaging sensor as one of the sensors described above, the stickable device 100 stuck under the user's eye can capture an image covering a field of view that approximately matches that of a user's viewpoint. Depending on an imaging optics, the stickable device 100 can capture an image covering a wider field of view than that of the user's viewpoint. Also, when installed under the left and right eyes, the stickable devices 100, each having an imaging sensor, can form a stereo camera. Needless to say, the stickable device 100 may be provided only under one of the eyes for use as a monocular camera.

Figure 9:
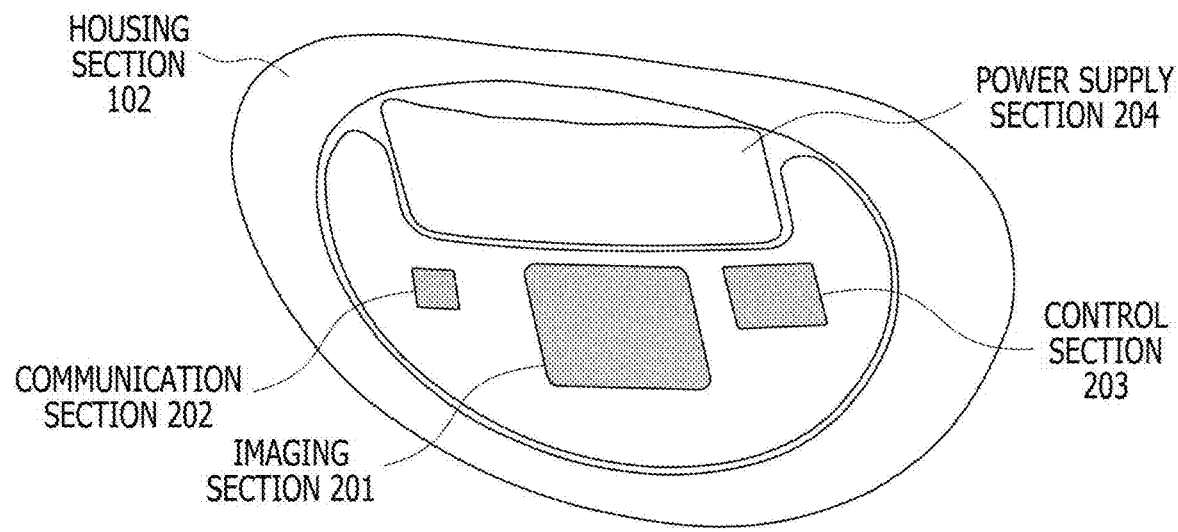
FIG. 9 is a diagram illustrating an example of an internal structure of the stickable device 100 that is stuck under the user's eye and that can function as a camera.

FIG. 9 illustrates an example of an internal structure of the stickable device 100 that is stuck under the user's eye and that can function as a camera. In FIG. 9, the sticking section 103 and the body fluid treatment section 104 are not depicted, and the stickable device 100 as seen from the rear side is illustrated. The electric section 101 includes an imaging section 201 as one of the sensors, a communication section 202, a control section 203, and a power supply section 204. The communication section 202 wirelessly communicates with external equipment. The control section 203 controls the imaging section 201 and the communication section 202. The power supply section 204 supplies power to at least one of the imaging section 201, the communication section 202, or the control section 203. These components are covered with the housing section 102. For example, it is possible to realize a wider viewing angle by providing a plurality of lensless imaging sensors without increasing the lens size or weight (which will be described later). In the configuration example illustrated in FIGS. 2 and 3 to 8, three holes are provided in the housing section 102 on the front surface to allow imaging with three imaging sensors.

Figure 10:
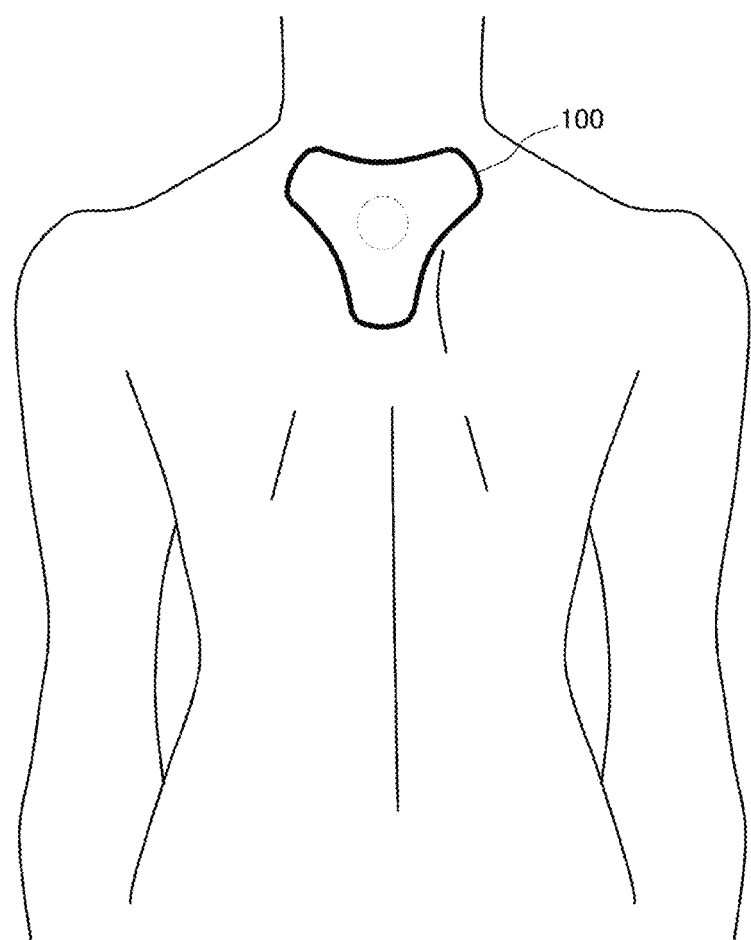
FIG. 10 is a diagram illustrating a manner in which the stickable device 100 is stuck to an upper center portion of a user's back.
Figure 11:
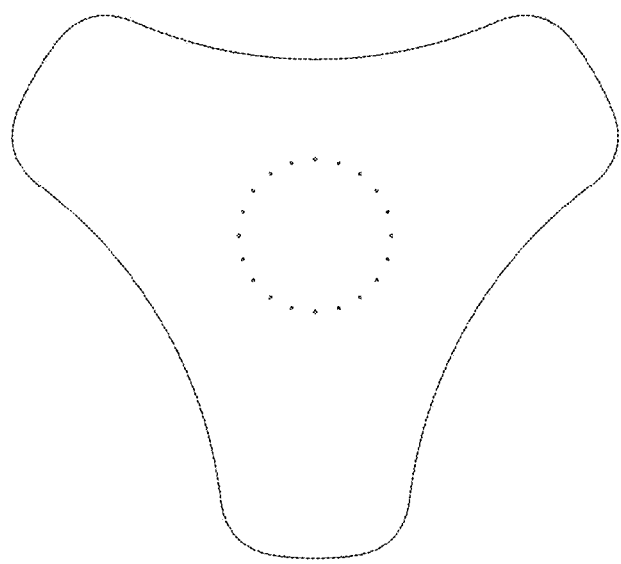
FIG. 11 is a front view of the stickable device 100 illustrated in FIG. 10.
Figure 12:
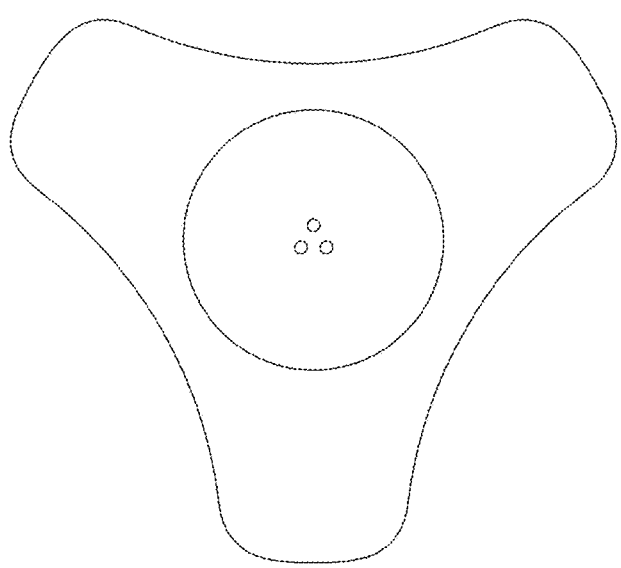
FIG. 12 is a rear view of the stickable device 100 illustrated in FIG. 10.
Figure 13:
FIG. 13 is a right-side view of the stickable device 100 illustrated in FIG. 10.
Figure 14:
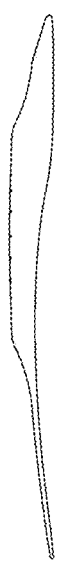
FIG. 14 is a left-side view of the stickable device 100 illustrated in FIG. 10.
Figure 15:
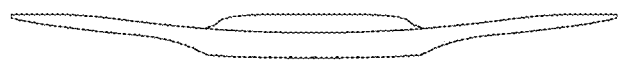
FIG. 15 is a top view of the stickable device 100 illustrated in FIG. 10.
Figure 16:
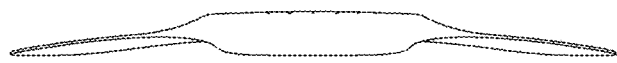
FIG. 16 is a bottom view of the stickable device 100 illustrated in FIG. 10.
Figure 17:
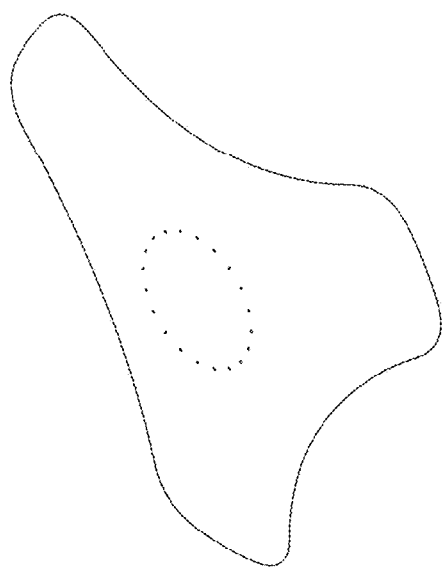
FIG. 17 is a perspective view of the stickable device 100 illustrated in FIG. 10.

FIG. 10 illustrates the stickable device 100 that is stuck to an upper center portion of the user's back as another example. Also, FIGS. 11 to 17 illustrate a front view, a rear view, a right-side view, a top view, a bottom view, and a perspective view of the stickable device 100 illustrated in FIG. 10, respectively. As is clear from FIG. 10 or 17, the outline of the type of the stickable device 100 stuck to the user's back includes a curve that facilitates the user's motion and readily fits with the curved surface of the body. If a radius r of the curve of the outline is excessively small (meaning an arc curve with a smaller radius), the location to which the stickable device 100 is stuck is small in area, resulting in insufficient strength for holding the main body of the stickable device 100. For this reason, the radius r of the curve has a magnitude that provides a moderate area. Also, if the outline of the stickable device 100 includes the moderate radius r of the curve, the stickable device 100 is covered with clothing when stuck to an upper portion of the back, making the stickable device 100 inconspicuous from outside as an advantageous effect.

Normally, the upper portion of the user's back is covered with clothing worn by the user, thus allowing the stickable device 100 to be used casually without giving any sense of discomfort to surrounding people. However, the stickable device 100 having an imaging sensor as the above sensor is not suited to capturing images of an outside world. On the other hand, because the user's body odor readily lingers on the back due to perspiration and metabolism, an odor sensor as one of the sensors described above may be included in the stickable device 100. Then, odor data (and chronological data of odor data) collected by the odor sensor may be wirelessly sent to external equipment by the communication section.

Also, there is a possibility that body odor may give a sense of discomfort to surrounding people or the user himself or herself. For this reason, the stickable device 100 stuck to the upper center portion of the user's back may further include an odor suppression section that has at least one of a fragrancing function or a deodorizing function. The control section need only control driving of fragrancing or deodorizing by the odor suppression section on the basis of the odor data collected by the odor sensor.

Figure 18:
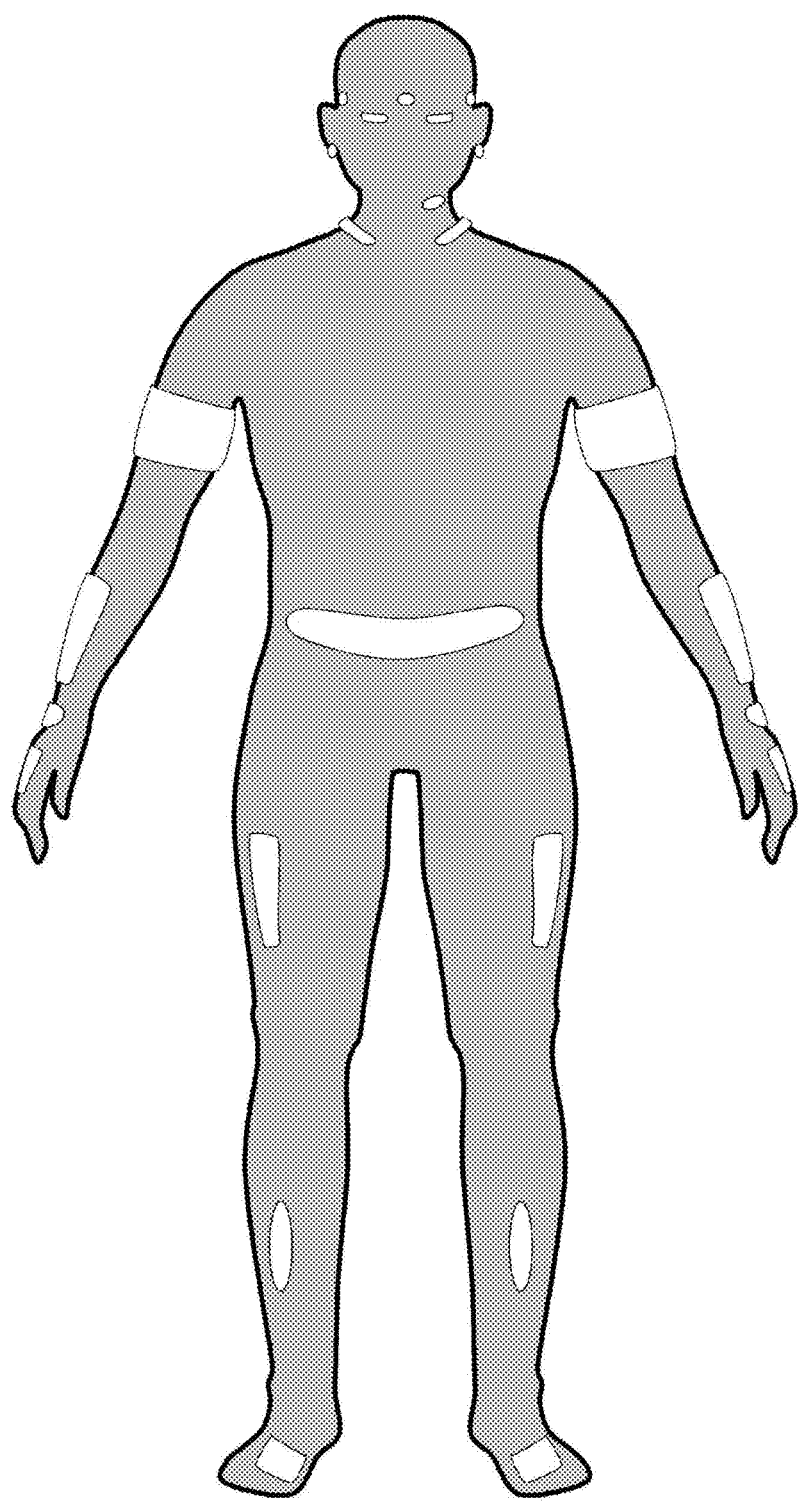
FIG. 18 is a diagram illustrating locations to which the stickable device proposed in the present specification can be stuck.

Although the stickable device 100 has been illustrated above that is stuck to each of the under-eye portions and the upper center portion of the back of the user for use, the main body of the stickable device 100 is assumably stuck to various locations on the surface of the user's body. FIG. 18 illustrates locations of the user's body to which the stickable device proposed in the present specification is assumably stuck. As illustrated, the stickable device is stuck to locations such as under the eye, the temple, middle of the forehead, back of the ear, under the chin, the neck, base of the neck, the throat, the upper arm, the forearm, the wrist, back of the hand, and the abdomen for use as a so-called wearable device.

It should be noted that although not illustrated, a similar stickable device can also be stuck not only to a human body but also to various animals (e.g., pet animals, livestock, working animals), plants (including plants grown as edible plants or house plants, and wild plants), and machines such as mobile objects for use as an IoT device.

Figure 19:
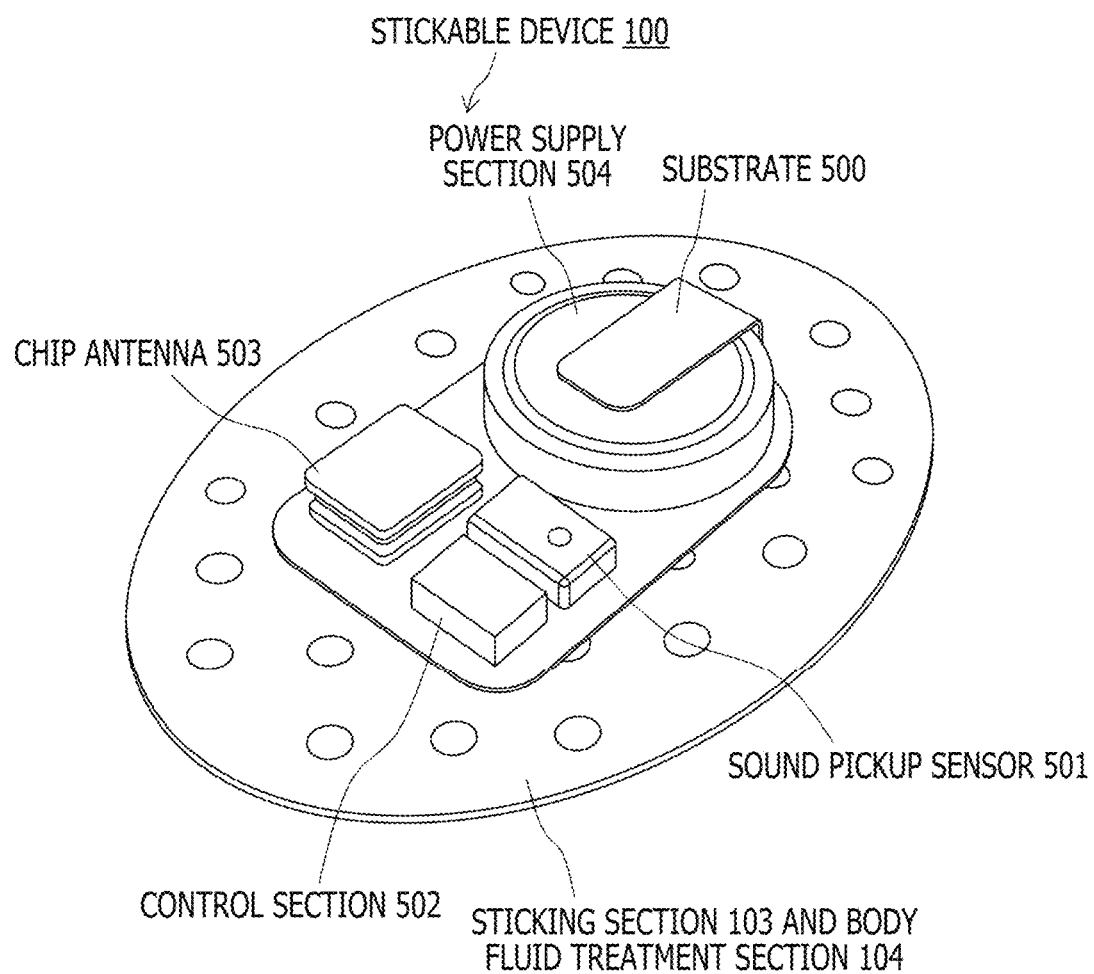
FIG. 19 is an exemplary diagram illustrating a manner in which an electric section 101 is mounted.

FIG. 19 illustrates a manner in which the electric section 101 is mounted to a substrate. A substrate 500 that is both flexible and expandable has not only a sensor 501 and circuit components such as a control section 502 and a chip antenna 503 but also a power supply section 504. The control section 502 serves also as a communication processing section. The power supply section 504 includes a coin battery.

Figure 20:
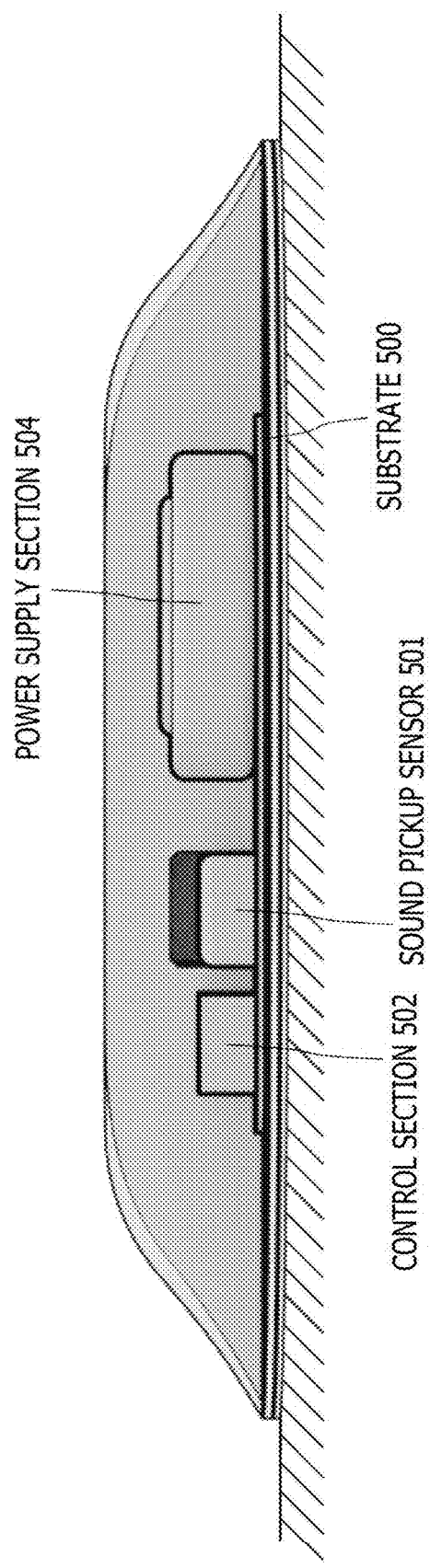
FIG. 20 is an exemplary diagram illustrating a sectional configuration of the stickable device 100 stuck to a user's body surface.

FIG. 20 illustrates a sectional configuration of the stickable device 100 stuck to the user's body surface. As has already been described with reference to FIG. 19, the flexible and expandable substrate 500 has not only the sensor 501 and circuit components such as the control section 502 but also the power supply section 504. The control section 502 serves also as a communication processing section. The power supply section 504 includes a coin battery.

Figure 21:
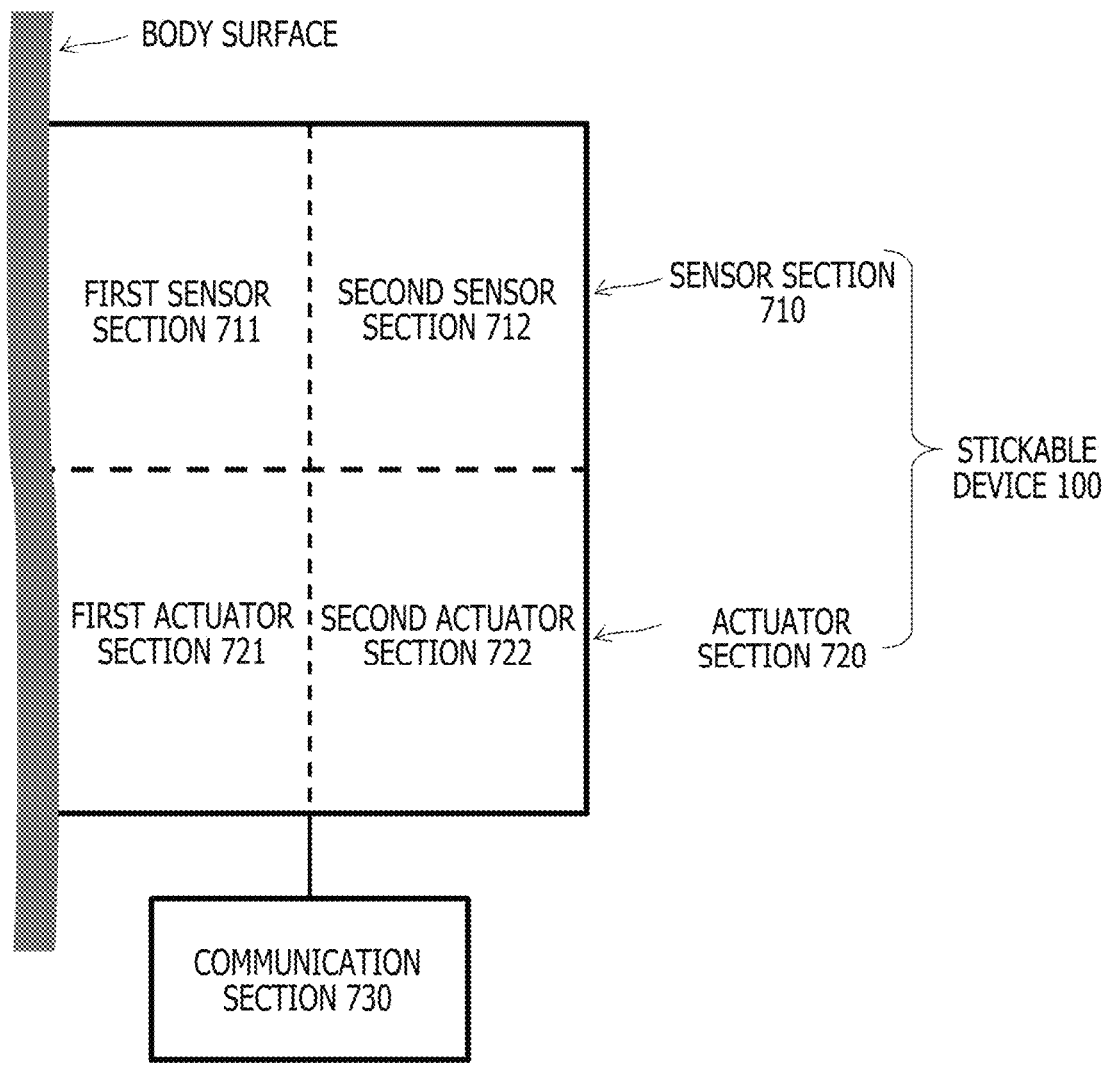
FIG. 21 is a diagram schematically illustrating a configuration example of an input/output function of the stickable device 100 stuck to the user's body surface for use.

FIG. 21 schematically illustrates a configuration example of an input/output function of the stickable device 100 stuck to the user's body surface for use. The stickable device 100 illustrated includes a sensor section 710, an actuator section 720, and a communication section 730.

The sensor section 710 includes a first sensor section 711 that detects user's human body information and a second sensor section 712 that detects information outside the user (outside world information). Both sections detect information by taking advantage of the feature brought about by contact of the main body of the stickable device 100 with the user's body surface. Also, the actuator section 720 includes a first actuator section 721 that outputs information to the user (human body) and a second actuator section 722 that outputs information outside the user (to the outside world and surrounding people).

As a basic function of the stickable device 100, the control section (not depicted in FIG. 21) drives at least one of the first actuator section 721 or the second actuator section 722 on the basis of detection results of at least one of a sound pickup sensor, the first sensor section 711, or the second sensor section 712. It is possible to notify the user of sensor data (e.g., user's own biological information or surrounding environment information) detected by the sensor by driving the first actuator section 721. Also, it is possible to notify people around the user of sensor's detection results by driving the second actuator section 722.

Also, as a function available with the stickable device 100, the control section wirelessly sends sensor data detected by the sensor section 710 to external equipment from the communication section 730 or drives the actuator section 720 on the basis of sensor data detected by the sensor section 710.

Also, as still another function available with the stickable device 100, the control section drives the actuator 720 on the basis of information received from external equipment via the communication section 730 and controls a detection procedure by the sensor section 710.

It should be noted that the control section may include a memory for storing an individual identification number that identifies the stickable device 100 (or a user), an encryption key used to prevent eavesdropping or the like during information exchange with external equipment, and other information. Also, the memory may temporarily store sensor data detected by the sensor section 710.

For example, the sound pickup sensor can be included in the first sensor section 711 from the viewpoint of picking up utterance of the user to whom the main body of the stickable device 100 is stuck. The sound pickup sensor picks up the sound produced by the user through air conduction from the mouth and flesh conduction or bone conduction in the head. A sound pickup hole should preferably be formed in the housing section 102 to pick up the sound conducted by air. Also, the sound pickup hole should preferably be waterproofed.

For example, in the case where the stickable device 100 is stuck, for use, to a location close to the mouth or vocal cords such as under the chin, the neck, base of the neck, or the throat, the sound pickup sensor can pick up minute voice information by means including air conduction from the mouth and flesh conduction or bone conduction in the head. Also, the sound pickup sensor can separate and pick up the user's voice even in a noise-exposed environment through flesh conduction or bone conduction.

In addition, the sound pickup sensor included in the first sensor section 711 and a speaker included in the first actuator section 721 can coordinate with each other to pick up, amplify, and reproduce sound, thus allowing the stickable device 100 to be used as a sound pickup or a hearing aid.

Also, an odor sensor for detecting the user's odor can be included in the first sensor section 711. Further, various types of biological sensors, which can detect biological information, can be included in the first sensor section 711 such as an electroencephalography sensor, a vein sensor, a myoelectric potential sensor, a body temperature sensor, a perspiration sensor, a heartbeat or pulse sensor, and a line-of-sight sensor. The control section may wirelessly send odor data (and chronological data of odor data) collected by the odor sensor and biological sensor data detected by another biological sensor to external equipment from the communication section 730. Also, the control section may control the driving of the actuator section 720 on the basis of odor data and other biological sensor data. For example, in the case where an odor suppression section is included as the second actuator section 722, the control section need only control the driving of fragrancing or deodorizing by the odor suppression section on the basis of the odor data collected by the odor sensor.

Also, in the case where the stickable device 100 is stuck to the user's head such as the temple or middle of the forehead, it is possible to detect the user's electroencephalography with high precision by using an electroencephalography sensor. The control section can realize a non-invasive Brain-Machine Interface (BMI) by analyzing detection results of the electroencephalography sensor and recognizing the user's will and emotion. Also, when sensing the user's drowsiness on the basis of detection results of the electroencephalography sensor, the control section can, for example, shake off drowsiness by an electric shock or the like by driving the first actuator section 721.

It should be noted, however, that the suitability of detection of biological information varies depending on the location to which the stickable device 100 is stuck, and the necessity for biological information varies depending on the intended use of the stickable device 100. Therefore, it is only necessary to incorporate a necessary biological sensor in the first sensor section 711 as appropriate in accordance with the location to which the stickable device 100 is stuck and the necessity for biological information.

Also, a vibration sensor can be included in the first sensor section 711. The vibration sensor includes, for example, an acceleration sensor, a gyro sensor, or a geomagnetic sensor, or a combination of two or more of these sensor elements. The control section can detect a posture or a body movement (e.g., impact, vibration, inclination, toppling, fall, movement) of the user to whose body the stickable device 100 is stuck on the basis of detection results of the vibration sensor. Also, in the case where the stickable device 100 is stuck to the user's back of the hand or the finger, for example, the control section can detect a gesture made by the user by analyzing detection results of the vibration sensor.

Further, the control section can extract feature data from vibration data detected by the vibration sensor and recognize the user's activity on the basis of a chronological order of a given amount of feature data accumulated (refer, for example, to PTL 2). Also, the control section may successively learn chronological information of the feature data. Vibration data obtained from the vibration sensor differs in feature from one location to which the main body of the stickable device 100 is stuck to another. For this reason, the control section can further estimate the location to which the main body of the stickable device 100 is stuck on the basis of vibration data (or chronological order of the feature data extracted from the vibration data) obtained from the vibration sensor.

Also, a sticking sensor can be included in the first sensor section 711. The sticking sensor detects whether the main body of the stickable device 100 is in a sticking state in which the main body of the stickable device 100 is stuck to the user's body by the sticking section 103. The sticking sensor can include, for example, a capacitive sensor that detects the change in capacitance as a result of the approach of a human body, an infrared reflection sensor that detects a reflected beam of infrared light that is emitted on a human body surface (skin), or other types of sensors.

The control section may control the activation of a given procedure of the stickable device 100 in accordance with the sticking state between the sticking section 103 and the user detected by the sticking sensor. For example, the control section may initiate the wireless transmission of sensor data detected by the sensor section 710 to external equipment in response to the detection, by the sticking sensor, of fastening of the main body of the stickable device 100 to the user with the sticking section 103. Also, in the case where the stickable device 100 further includes a host device that wirelessly communicates via the communication section, sensor data detected by the sensor section 710 may be wirelessly sent to the host device, and the host device may perform an authentication procedure of the user on the basis of the sensor data. Also, the control section may notify the user by driving the actuator section 720 or wirelessly send a given signal to the host device, for example, in response to detection, by the sticking sensor, of the fact that the sticking section 103 has begun to peel off from the user or is just about to peel off from the user. The host device may cancel the user authentication established by the authentication procedure as a result of the reception of the given signal. The host device may be, for example, an information terminal owned by the user such as a smartphone.

A sound pickup sensor (e.g., microphone) that picks up acoustics or noise in an outside world (rather than the user's real voice), an imaging sensor that captures images of a surrounding landscape, an environmental sensor that detects information regarding outside environment such as temperature, humidity, illuminance, and atmospheric pressure can be cited as examples of the second sensor section 712. The stickable device 100 stuck under the user's eye as illustrated in FIG. 2 can capture an image covering a field of view that approximately matches that of a user's viewpoint. Depending on the imaging optics, the stickable device 100 can capture an image covering a wider field of view than that of the user's viewpoint. Also, when installed under the left and right eyes, the stickable devices 100, each having an imaging sensor, can form a stereo camera. The control section may wirelessly send, in real time, an image captured from under the user's eye to external equipment, for example.

The chip antenna 503 for wireless communication (described earlier) can be included in the second sensor section 712 in a broad sense from the viewpoint of detecting radio waves (wireless signals). Further, a position information sensor such as a GPS (Global Positioning System) sensor can be included in the second sensor section 712. It should be noted, however, that the stickable devices 100 can be equipped with a position detection function by means other than a position information sensor. For example, in the case where an image sensor is provided as the second sensor section 712, self-position estimation can be realized by using SLAM (Simultaneous Localization and Mapping), ToF (Time of Flight), or other technologies. Also, the current position can be calculated on the basis of a balance of intensities of radio waves received by the chip antenna 503 from a plurality of surrounding access points by using a PlaceEngine technology. In the case where a position information sensor is provided as the second sensor section 712, or in the case where the stickable device 100 has a position detection function, the control section can recognize the user's activity on the basis of the chronological order of the user's position information, i.e., route information.

It should be noted, however, that the suitable task to be performed by the sensor element varies depending on the location to which the stickable device 100 is stuck. For example, in the case where the main body of the stickable device 100 is stuck under the user's eye as illustrated in FIG. 2, capturing an image of a surrounding landscape is a suitable task. However, in the case where the main body of the stickable device 100 is stuck under the chin, capturing an image of a surrounding landscape is not a suitable task. Therefore, it is only necessary to incorporate a necessary sensor element in each first sensor section 711 and second sensor section 712 as appropriate in accordance with the location to which the stickable device 100 is stuck and the necessity for biological information.

The first actuator section 721 basically directly produces an output to the user's body. For example, a compact speaker, a flesh conduction speaker that produces sounds through flesh conduction, a haptic device capable of haptic output, a vibration actuator that applies a vibration stimulus, an actuator that gives a slight electric stimulus (or a device that outputs an extremely small current), and so on can be cited as examples of the first actuator section 721. It should be noted, however, that the suitability of output varies depending on the location to which the stickable device 100 is stuck, and that the necessity for biological information varies depending on the intended use of the stickable device 100 itself. Therefore, it is only necessary to incorporate a necessary actuator element in the first actuator section 721 as appropriate in accordance with the location to which the stickable device 100 is stuck and the necessity for information output.

The second actuator section 722 basically outputs information to the user wearing the stickable device 100 and surrounding people. Information provided from external equipment such as the host device received via the communication section 730 can be cited as an example of information output from the second actuator section 722.

For example, a display section that outputs light or images and a speaker that produces sounds can be cited as examples of the second actuator section 722. The display section can include, for example, a highly flexible organic EL (Electro Luminescence) display. The display section is not accommodated in the housing 102 and, instead, is disposed on the surface of the housing 102. Also, in the case where a speaker is provided as the second actuator section 722, an acoustic output hole or an exhaust hole is formed on the surface of the housing 102 in some cases.

Also, it is possible to output, from the first actuator section 721 and the second actuator section 722, detection results of the first sensor section 711 and the second sensor section 712 and results obtained by analyzing or recognizing the detection data by the control section. For example, in the case where a sticking sensor is included as the first sensor section 711, the control section may notify the user by driving the actuator section 720 in response to detection, by the sticking sensor, of the fact that the sticking section 103 has begun to peel off from the user or is just about to peel off from the user, for example. Also, in the case where an odor sensor is included as the first sensor section 711, the control section may perform fragrancing, deodorizing, or other procedures by driving the odor suppression section included in the second actuator section 722 in response to the detection of the user's body odor by the odor sensor.

It should be noted, however, that the suitability of output varies depending on the location to which the stickable device 100 is stuck, and that the necessity for output varies depending on the intended use of the stickable device 100 itself. Therefore, it is only necessary to incorporate a necessary actuator element in each first actuator section 721 and second actuator section 722 as appropriate in accordance with the location to which the stickable device 100 is stuck and the necessity for information output.

The communication section 730 communicates information with external equipment such as the host device. For example, the communication section 730 outputs sensor data detected by the sensor section and 10 to external equipment.

Also, the communication section 730 inputs an instruction from external equipment to the control section or to the actuator section 720.

The communication section 730 communicates with the host device or apparatuses on the Internet (e.g., cloud) by way of wireless communication such as Wi-Fi. Alternatively, the communication section 730 communicates with other information terminals owned by the user such as a smartphone by using other short-range communication function such as Bluetooth (registered trademark). When the communication section 330 wirelessly communicates information with external equipment, secret communication is preferred by using an encryption key to prevent eavesdropping (described earlier).

Also, the communication section 730 may communicate with or perform an authentication procedure of information terminals at a close range by using a proximity wireless communication technology such as NFC (Near Field Communication). Also, the communication section 730 may include a human body communication function, and may communicate information with other stickable devices stuck to other body locations of the same user or with an information terminal owned by the same user by way of human body communication.

Sensor elements applicable to the first sensor section 711 and the second sensor section 712 and actuator elements applicable to the first actuator section 721 and the second actuator section 722 also depend on the location to which the main body of the stickable device 100 is stuck. The suitability of sensor elements and actuator elements in accordance with the location to which the stickable device 100 is stuck is summarized in FIG. 22.

Two possible options are available for configuring the stickable device 100. In one option, the stickable device 100 is stuck to a limited number of locations so that only a minimal number of sensor elements and actuator elements are provided. In another option, as many types of sensor elements and actuator elements as possible are provided assuming that such elements are applied to a number of locations, thus forming the high-spec stickable device 100.

The former approach allows for manufacture of each of the stickable devices 100 relatively inexpensively. As a result, the stickable device 100 can be used as a disposable device. For example, the stickable device 100 that has peeled off from the user's body once is disposed of as expired.

Also, the latter approach leads to sensor elements and actuator elements that need not be activated depending on the actual locations to which these elements are stuck. Driving all the sensor elements and actuator elements results in wastage of power. For this reason, each of the sensor elements and actuator elements may be turned on and off manually. Alternatively, the control section may control the sensor elements and actuator elements to turn on and off automatically by estimating the locations to which these elements are stuck on the basis of vibration data (user's body movement) acquired from the vibration sensor or sensor data acquired from the biological sensor or other sensors. Also, the control section may perform control such as changing sensor sensitivities step by step or changing actuator output levels step by step, in accordance with the intended use of the stickable device 100 estimated by the location to which the stickable device 100 is stuck, rather than controlling complete on and off switching of each of the sensor elements and the actuator elements.

It should be noted that proposals have already been made regarding a skin patch material that incorporates a temperature sensor and that is stuck to the skin of a specimen such as human for use (refer, for example, to PTL 3). Although incorporating, in addition to the temperature sensor, electric sections such as microprocessor and transmitter and a button battery, this skin patch material does not have a sticking sensor. That is, this skin patch material is essentially different from the stickable device disclosed in the present specification from the viewpoint that the skin patch material cannot wirelessly send a given signal to external equipment via the communication section in response to detection, by the sticking sensor, of the fact that the sticking section has begun to peel off from the user or is just about to peel off from the user, and from the viewpoint that the skin patch material cannot notify the user, for example, that the sticking section has begun to peel off from the user or is just about to peel off from the user.

B. Protection of the Sticking Surface and a Sequence for Initiating the Use of the Apparatus Regardless of where the stickable device 100 is stuck for use, the stickable device 100 is assumably distributed in a protected manner so as to keep the adhesive surface of the sticking section 103 free from dust and other foreign matters and maintain the adhesive performance of the sticking section 103. Specifically, when unused, the adhesive surface of the sticking section 103 is protected with release paper.

Also, the amount of time from the shipment of the stickable device 100 to the start of its use is unknown. It is necessary to maintain the adhesive performance of the sticking section 103 as described above, and avoid or suppress exhaustion of the battery used as the power supply section 504 for extended periods until the start of its use.

For this reason, in the present embodiment, a non-conductive section is formed in part of the release paper used to protect the adhesive surface of the sticking section 103, thus allowing, when the adhesive surface is protected with the release paper, for storage while simultaneously maintaining the power supply section 504 insulated from the substrate 500 by the non-conductive section or maintaining a non-conductive state. Then, peeling off the release paper from the adhesive surface at the start of the use of the stickable device 100 allows for the main body of the stickable device 100 to be stuck to a given location of the user's body. At the same time, power can be supplied from the power supply section 504 to each circuit component of the substrate 500, thus allowing the stickable device 100 to initiate its operation.

Figures 22, 23:
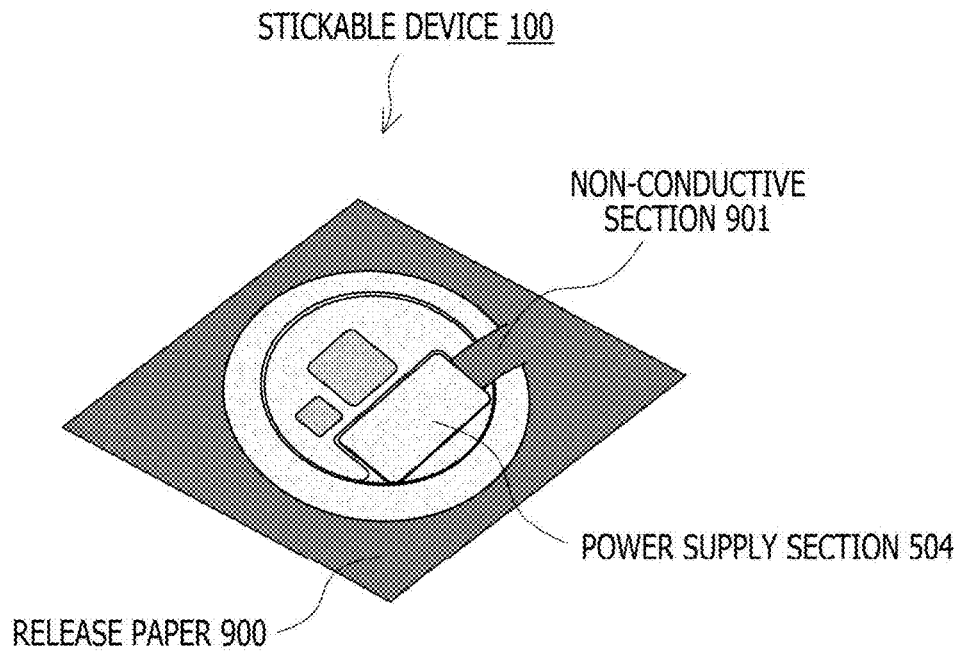
FIG. 22 is a diagram illustrating whether or not sensor elements and actuator elements are suitable for sticking depending on where the stickable device 100 is stuck.
FIG. 23 is a diagram illustrating a manner in which a piece of release paper 900 is stuck to an adhesive surface of a sticking section 103 of the stickable device 100 to protect the adhesive surface.

FIG. 23 illustrates a manner in which a piece of release paper 900 is stuck to an adhesive surface of the sticking section 103 of the stickable device 100 to protect the adhesive surface. It should be noted, however, that FIG. 23 depicts that the substrate 500 is exposed with the housing section 102 removed for ease of viewing.

A non-conductive section 901 in the shape of a tongue piece is formed in part of the release paper 900. With the release paper 900 attached to the sticking section 103 (not depicted in FIG. 23) on the rear side of the substrate 500, the non-conductive section 901 is inserted into a gap between the power supply section 504 and the substrate 500, thus maintaining the two insulated from or non-conductive to each other. It should be noted, however, that at least the portion of the non-conductive section 901 in the shape of a tongue piece of the release paper 900 includes, as a precondition, an insulating material.

Then, when the release paper 900 is peeled off at the start of the use of the stickable device 100, the adhesive surface of the sticking section 103 is exposed, thus allowing the stickable device 100 to be stuck to a given location of the user's body. At the same time, the non-conductive section 901 is pulled out of the gap between the power supply section 504 and the substrate 500, thus making it possible to supply power to each circuit component of the substrate 500 from the power supply section 504 and initiate the operation of the stickable device 100.

As described above, the power for the stickable device 100 is off while it is stored in a manner protected with the release paper 900, and when the release paper 900 is removed, the stickable device 100 begins its operation.

It should be noted that the power-off state is not limited to a state in which power is completely shut off by means such as the non-conductive section 901 and may be a sufficiently power-saving state as a modification. The stickable device 100 can, in a sufficiently power-saving state, activate part of the sensor section 710 such as the sticking sensor, thus monitoring the presence or absence of light reflection, measuring an impedance of the sticking surface (adhesive surface) of the sticking section 103, monitoring environmental changes such as temperature, humidity, and illuminance, and monitoring changes in biological information such as blood flow. Then, when the fact that the use of the stickable device 100 is just about to begin is detected in response to a piece of sensor data or composite information including a plurality of pieces of sensor data, the stickable device 100 may switch from a power-saving state to a power-on state and be on standby until it is stuck to a given location of the user's body.

Regardless of whether the use of the stickable device 100 begins in response to the removal of the non-conductive section 901 or change in sensor data, when the sticking of the stickable device 100 to the user's body is detected, it is possible to acquire user's biological information and authenticate the user on the basis of the biological information.

The state of sticking to the user can be detected, for example, by the sticking sensor included in the first sensor section 711 on the basis of sensor data such as temperature, humidity, illuminance, blood flow state, or blood vessel shape, or change in sensor data, composite information including two or more pieces of sensor data, and so on. Alternatively, the sticking sensor can detect the sticking state on the basis of change in capacitance as a result of approach of a human body or a reflected beam of infrared light that is emitted on a human body surface (skin).

Also, the user authentication can be confirmed by comparing a feature quantity of biological information detected mainly by the first sensor section 711 with biological information acquired from the user in advance. Blood vessel shape on the sticking surface, body fluid information, skin pigment information, or other information can be, for example, used as biological information.

It should be noted that the number of sensor elements provided on the stickable device 100 can be saved by using the same biological information for detecting the sticking state and authenticating the user. Also, when biological information for authenticating the user cannot be acquired, the sticking state is not detected in the first place. Thus, an unnecessary usage initiation procedure need not be performed.

In the case where the stickable device 100 further includes a host device capable of wireless communication via the communication section 730, an equipment authentication and a user authentication can be carried out effectively and highly accurately using the host device at the start of the use of the stickable device 100 following the sticking to the user's body by registering equipment information of the stickable device 100 and user authentication information (e.g., feature quantity of biological information) in the host device in advance.

The control section controls the operation of the stickable device 100 in response to the sticking state of the main body of the stickable device 100. When the stickable device 100 is not stuck to the user's body surface although the release paper 900 has been peeled off from the adhesive surface of the sticking section 103, the stickable device 100 can be considered unused. Therefore, even if the power supply section 504 is ready for supplying power to each section of the substrate 500 following the removal of the non-conductive section 901 as a result of the peeling-off of the release paper 900 from the adhesive surface of the sticking section 103, the control section suspends the operation of the circuitry with the exception of some of the functions including the sticking sensor and remains on standby until the use of the stickable device 100 begins in a sufficiently power-saving state. Then, when the sticking of the stickable device 100 to the user's body is detected, the control section switches the stickable device 100 from a power-saving state to a power-on state, thus activating the circuits and functions that have been inactive. The control section may activate given procedures such as the authentication procedure after switching the stickable device 100 to a normal power-on state.

Figure 24:
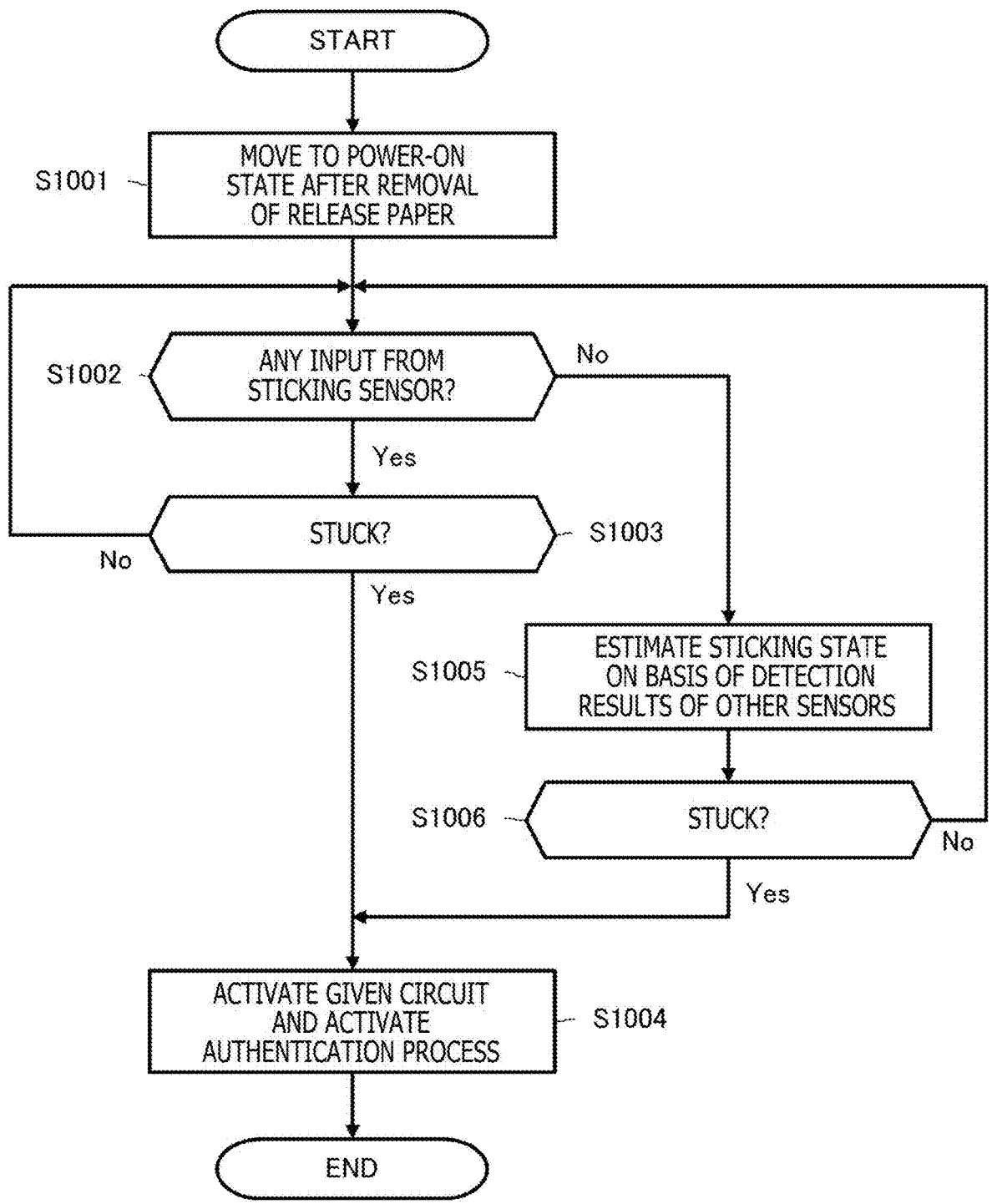
FIG. 24 is a flowchart illustrating a processing sequence for activating the stickable device 100 in response to a state of sticking to the user's body.

FIG. 24 illustrates, in a flowchart form, a processing sequence for activating the stickable device 100 in response to the state of sticking to the user's body. The processing sequence illustrated is carried out, for example, under the initiative of the control section of the stickable device 100.

When the non-conductive section 901 is pulled out as a result of the peeling-off of the release paper 900 from the adhesive surface of the sticking section 103 of the stickable device 100, the electric section 101 begins to conduct (step S1001). Then, some of the circuits and sensor elements including the control section initiate their operation.

Then, the control section checks whether there has been any input from the sticking sensor (step S1002).

When there is an input from the sticking sensor (Yes in step S1002), the control section further checks whether the stickable device 100 has been stuck to the user's body and has switched to an in-use state (step S1003).

Here, when there is no input from the sticking sensor (No in step S1002), the control section attempts to determine the sticking state of the stickable device 100 on the basis of sensor data detected by sensors other than the sticking sensor (e.g., other sensor elements included in the first sensor section 711 such as a biological sensor and a vibration sensor) (step S1005).

Then, when it is found out that the main body of the stickable device 100 is stuck to the user's body (Yes in step S1003), or when it is estimated that the main body of the stickable device 100 is stuck (Yes in step S1005), the control section switches the stickable device 100 from a power-saving state to a normal power-on state, thus activating the circuits and functions that have been inactive. Then, the control section activates given procedures such as the authentication procedure (step S1004).

On the other hand, when it is found out that the main body of the stickable device 100 is not stuck to the user's body on the basis of sensor data detected by the sticking sensor (No in step S1003), or when it is estimated that the main body of the stickable device 100 is not stuck on the basis of sensor data detected by a sensor other than the sticking sensor (No in step S1006), the procedure returns to step S1002, and the above procedures are repeated until the main body of the stickable device 100 is stuck to the user's body.

The term "authentication" here includes either one or both of two procedures including a procedure for authenticating the user himself or herself to whom the main body of the stickable device 100 is stuck and a procedure for authentication with other equipment. In the former user authentication, for example, biological information detected by a biological sensor may be used. Also, the electric section 101 may include anti-tampering circuit components such as IC chips to realize authentication procedures without fraud. For example, information regarding remote pairing may be written by using an embedded IC card such as an eSIM. Also, the control section may pair with other pieces of equipment in the course of the authentication procedure.

Figure 25:
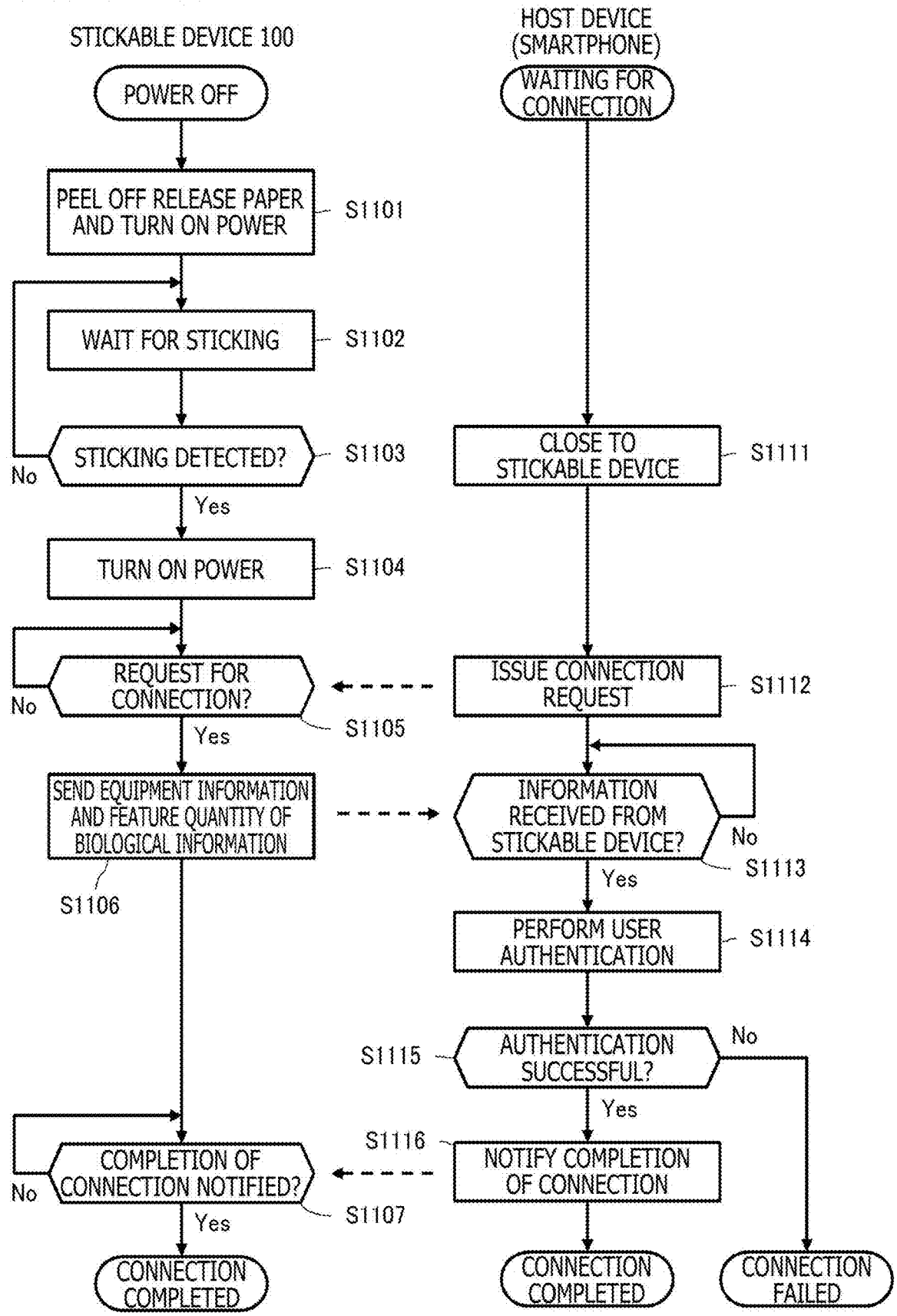
FIG. 25 is a flowchart illustrating another processing sequence for activating the stickable device 100 in response to a state of sticking to the user's body.

Also, FIG. 25 illustrates, in a flowchart form, another processing sequence for activating the stickable device 100 in response to the state of sticking to the user's body. The processing sequence illustrated assumes that the stickable device 100 further includes a host device that wirelessly communicates via the communication section, and the stickable device 100 proceeds with the authentication procedure and pairing with the host device. The host device may be, for example, an information terminal owned by the user such as a smartphone.

When the non-conductive section 901 is pulled out as a result of the peeling-off of the release paper 900 from the adhesive surface of the sticking section 103 of the stickable device 100, the electric section 101 begins to conduct (step S1101). Then, some of the circuits and sensor elements including the control section initiate their operation.

When the conduction begins, the stickable device 100 remains in a wait state for detection of the sticking (step S1102) until the sticking of the stickable device 100 to the user's body is detected or estimated (No in step S1103). In a wait state, the control section detects whether the stickable device 100 has been stuck to the user's body on the basis of sensor data detected by the sticking sensor or estimates whether the stickable device 100 has been stuck to the user's body on the basis of sensor data detected by a sensor other than the sticking sensor.

Then, when it is found out that the main body of the stickable device 100 is stuck to the user's body, or when it is estimated that the main body of the stickable device 100 is stuck (Yes in step S1103), the control section switches the stickable device 100 from a power-saving state to a normal power-on state (step S1104), thus activating the circuits and functions that have been inactive (same as described above).

On the other hand, it is assumed that the host device that includes, for example, a smartphone is in a wait state for connection with the stickable device 100 stuck to the user's body.

Also, in the present procedure, the user carries, as a precondition, the host device at all times. Therefore, the host device is inevitably in proximity to the stickable device 100 stuck to the user's body (step S1111).

The host device issues a connection request to the stickable device 100 by using proximity communication (step S1112). The term "proximity communication" here refers to communication means available with the communication section 730 on the side of the stickable device 100. Specifically, the host device issues a connection request to the stickable device 100 by using Wi-Fi, Bluetooh (registered trademark), NFC, human communication, or other means.

On the other hand, when a connection request from the host device is received (Yes in step S1105), the stickable device 100 sends its own equipment information and the feature quantity of the user's biological information detected by the first sensor section 711 to the host device (step S1106) and remains in a wait state for a notice from the host device (No in step S1107).

When the equipment information and the feature quantity of the user's biological information are received from the stickable device 100 to which a connection request has been made (Yes in step S1113), the host device proceeds with the equipment authentication of the stickable device 100 and the user authentication (step S1114).

For example, it is possible to carry out personal authentication by using biological information such as motion, myoelectric potential, and heartbeat of the user to whom the stickable device 100 is stuck. A personal authentication technique based on a heartbeat signal is already known (refer, for example, to PTL 4). The host device carries out the authentication procedure of the stickable device 100 by comparing with equipment information and the feature quantity of the user's biological information registered in advance.

Then, when the authentication procedure succeeds (Yes in step S1115), the host device notifies the completion of connection to the stickable device 100 (step S1116) and terminates the present procedure. Also, when the authentication procedure fails (No in step S1115), the host device considers that a connection attempt with the stickable device 100 has failed and terminates the present procedure.

When a connection completion notice is received from the host device (Yes in step S1107), the stickable device 100 terminates the present procedure and remains in a connected state with the host device. It should be noted that in the case where a connection completion notice cannot be received from the host device within a given time period (that is, a timeout occurs), the stickable device 100 may consider that a connection attempt with the host device has failed and terminate the present procedure.

In the connection sequence illustrated in FIG. 25, the authentication procedure may be performed in a given time period after the detection of sticking of the stickable device 100 to the user's body rather than immediately after the detection. The stickable device 100 can acquire sensor data detected by the sensor section 710 for the given time period after the detection of the sticking and carry out a more accurate user authentication on the basis of the sensor data spanning the given time period. For example, the stickable device 100 can identify the user from user's habits by extracting, for the given time period from the detection of the sticking, the feature quantity from motion information such as user's body acceleration and angular velocities of his or her joints and biological information such as myoelectric potential and heartbeat, and by comparing with the user's inherent feature quantity.

The stickable device 100 and the host device, which have been connected each other, are set to a ready-to-use state. The stickable device 100 and the host device that have been connected can also be said to be in a "paired" state, thus allowing the two to perform various tasks in a coordinated fashion.

In the processing sequence illustrated in FIG. 25, the stickable device 100 and the host device are paired by using a communication sequence based on a proximity communication technology. However, the means used for pairing is not particularly limited. For example, the devices can be paired directly by using a QR code (the host device reads the QR code attached to the stickable device 100 or the stickable device 100 reads the QR code attached to the host device). Also, the stickable device 100 may be equipped with an embedded IC card such as an eSIM so that pairing information can be remotely written.

The host device can send a variety of types of operation commands to the paired stickable device 100 by using proximity communication (described earlier). On the other hand, the stickable device 100 can send sensor data detected by the sensor section 710 to the host device by using proximity communication (described earlier).

In the case where the host device is an information terminal such as a smartphone, the user can remotely control the stickable device 100 by inputting an operation command into the stickable device 100 via the smartphone screen. Needless to say, the user can directly manipulate the stickable device 100 via the sensor sections, switches, and so on provided on the stickable device 100 without using the host device. Also, the stickable device 100 can send, to the host device, biological information detected by the biological sensor included in the first sensor section 711 and sensor data such as an image of the surrounding landscape captured by the imaging sensor included in the second sensor section 712, thus allowing the host device side to store the received sensor data or display the data on the screen.

Also, the plurality of stickable devices 100 stuck to the body of the same user can coordinate with each other by connecting to a single host device. Needless to say, the plurality of stickable devices 100 stuck to the body of the same user can coordinate with each other through direct communication without using the host device. In the case where the plurality of stickable devices 100 coordinate with each other, one possible option would be that the stickable devices 100 initiate their operation only after the authentication procedures of all the stickable devices 100 are finished. Another possible option would be that each of the stickable devices 100 initiates its operation individually for scalable expansion of functions.

Also, coordination between the plurality of stickable devices 100 stuck to the plurality of locations of the user's body makes it possible to grasp motion data regarding user's activity and body motion with high accuracy. For example, the stickable devices 100 stuck under the user's left and right eyes and each including the imaging sensor can coordinate with each other to function as a stereo camera. The user's motion can be grasped with even higher accuracy by combining motion data with myoelectric potential data. Realization of highly accurate motion capture allows for detection of gestures made by the user, thus making it possible to input gesture-based commands.

It should be noted that the procedure performed by the host device in FIG. 25 may be handled by using a cloud (or computer resources on a wide-area network) rather than an information terminal such as a smartphone carried by the user. Authentication requests accompanied by biological information or the like are assumably sent from the plurality of users. In such a case, the cloud side prepares a signature on the basis of biological information sent from the first stickable device 100 stuck to a certain user and stores the signature in association with the user. Then, when biological information is sent from the second and subsequent stickable devices 100 stuck to the same user, the cloud side can associate (e.g., pair) the plurality of stickable devices 100 stuck to the same user on the basis of biological information by performing a user authentication through matching with the signature stored already.

C. Peeling Off (Unsticking) the Apparatus and Halting its Use

When halting the operation or terminating the use of the stickable device 100 stuck to his or her own body, the user need only halt the stickable device 100 by manipulation via the host device. Alternatively, the user can normally terminate the operation of the stickable device 100 by peeling off (or unsticking) the stickable device 100 from his or her body.

Also, the user assumably leaves the stickable device 100 whose use has been terminated after having peeled it off from his or her body, unattended. Alternatively, the stickable device 100 stuck to the user's body and being in use assumably peels off from the user against the user's intension without being noticed by the user at that time, thus causing the stickable device 100 that has peeled off to be left unattended. FIG. 1 illustrates an exemplary manner in which a stickable device stuck under the user's eye is about to peel off.

There is a possibility that information stored in the stickable device 100 that has peeled off may leak out. For example, equipment information stored in the stickable device 100 and sensor data detected by the sensor section 710 face a risk of leakage to external equipment. Equipment information includes security information and user's personal information. Also, sensor data includes user's personal information such as biological information, thus resulting in a risk of invasion of privacy. For this reason, in the present embodiment, at least part of information stored in the stickable device 100 that has peeled off from the user's body or is just about to peel off from the user's body is initialized or deleted, thus preventing leakage to external equipment.

Also, if the host device leaves the stickable device 100 in an authenticated state even after the stickable device 100 has peeled off from the user's body, there is a possibility that the authenticated state may be abused including fraudulent access of an unauthorized user to the host device by using the stickable device 100 without permission, for example. For this reason, in the present embodiment, the host device cancels the authenticated state of the stickable device 100 that has peeled off from the user's body or is just about to peel off from the user's body, thus preventing fraudulent use of the stickable device 100 that has peeled off. Also, in the present embodiment, the host device notifies the user that the stickable device 100 has peeled off from the user's body or is just about to peel off from the user's body, thus alerting the user to a potential risk of fraudulent use. In the case where the peeling-off of the stickable device 100 is not intended, the user can become aware of the notice and take a measure such as sticking the stickable device 100 again.

Also, in the present embodiment, in order to allow the host device side to perform a procedure as described above to deal with the peeling-off of the stickable device 100, the stickable device 100 notifies the host device that the stickable device 100 has peeled off or is just about to peel off.

Figure 26:
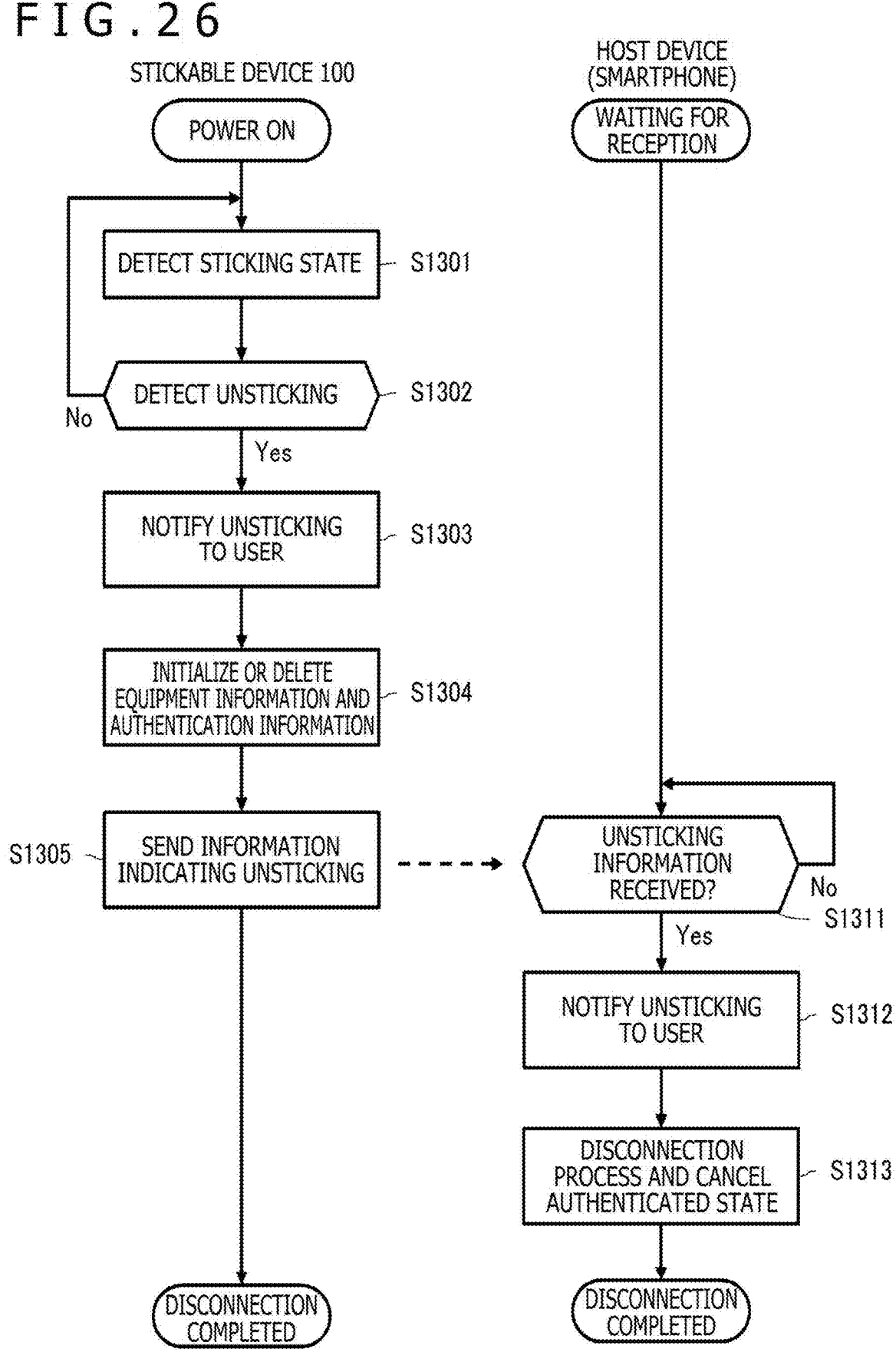
FIG. 26 is a flowchart illustrating a processing sequence for peeling off the stickable device 100 stuck to the user's body.

FIG. 26 illustrates, in a flowchart form, a processing sequence to be followed by the stickable device 100 and the host device when the user peels off the stickable device 100 stuck to the user's body.

The side of the stickable device 100 detects the state of sticking to the user's body constantly or regularly on the basis of sensor data detected by the sticking sensor or another sensor (step S1301).

Then, when the fact that the stickable device 100 has peeled off from the user's body or is just about to peel off from the user's body (i.e., unsticking) is detected (Yes in step S1302), the control section initializes or deletes at least part of the information stored in the stickable device 100 (step S1304), thus preventing leakage to external equipment. Information to be initialized or deleted includes, for example, equipment information, user's personal information, user's biological information detected by the biological sensor, and so on.

Here, two cases are possible, one in which the user attempts to peel off the stickable device 100 from his or her body by himself or herself and another in which the stickable device 100 peels off without the user's intention because of a reduced adhesion capability of the adhesive surface of the sticking section 103. For this reason, the stickable device 100 may alert the user by notifying the user that the stickable device 100 has peeled off or is just about to peel off (step S1303). For example, the user can be notified by driving the first actuator section 721 or the second actuator section 722. The user may be notified before initialization or deletion of information in step S1304 or after initialization or deletion of information.

Next, the control section of the stickable device 100 sends, to the host device via the communication section 730, information indicating that the stickable device 100 has peeled off from the user's body or is just about to peel off from the user's body (i.e., unsticking) (step S1305). The stickable device 100 completes the disconnection procedure from the host device after the transmission of this information.

On the other hand, the host device side remains, for example, in a wait state for signal reception from the stickable device 100 after the completion of connection with the stickable device 100 in accordance with the processing sequence illustrated in FIG. 25.

Then, when information indicating that the stickable device 100 has peeled off from the user's body or is just about to peel off from the user's body, which is sent from the stickable device 100 in the above step S1305, is received (Yes in step S1311), the host device activates the disconnection procedure from the stickable device 100 and cancels the authenticated state of the stickable device 100 (step S1313), thus preventing fraudulent use of the stickable device 100 that has peeled off.

Here, two cases are possible, one in which the user attempts to peel off the stickable device 100 from his or her body by himself or herself and another in which the stickable device 100 peels off without the user's intention because of a reduced adhesion capability of the adhesive surface of the sticking section 103. For this reason, the host device may alert the user by notifying the user that the stickable device 100 has peeled off or is just about to peel off (step S1312). For example, in the case where the host device is a smartphone, the fact that the stickable device 100 has peeled off or is just about to peel off is displayed on the smartphone screen. Alternatively, the fact that the stickable device 100 has peeled off or is just about to peel off is output as a voice message. The user may be notified before the cancellation of the authenticated state in step S1313 or after the cancellation of the authenticated state.

Then, after having cancelled the authenticated state of the stickable device 100, the host device completes the disconnection from the stickable device 100. It should be noted that the host device also cancels the association (pairing) with other stickable devices concurrently with the cancellation of the authenticated state of the stickable device 100 that has notified the unsticking and the disconnection therefrom.

It should be noted that the sticking sensor of the stickable device 100 includes, for example, a capacitive sensor that detects the change in capacitance as a result of the approach of a human body, an infrared reflection sensor that detects a reflected beam of infrared light that is emitted on a human body surface (skin), or other types of sensors and can detect whether the stickable device 100 has peeled off from the user's body. Also, it is possible to detect whether the stickable device 100 has peeled off from the user's body by monitoring environmental changes such as temperature, humidity, and illuminance or monitoring changes in biological information such as blood flow.

On the other hand, it is difficult to detect a state in which the stickable device 100 has yet to completely peel off from the user's body and is just about to peel off, in other words, is almost peeling off. For this reason, in a state where the stickable device 100 is almost peeling off from the user's body and, therefore, is blowing off, the state of almost peeling off may be detected by deep-learning sensor data detected by the vibration sensor, or other data.

Also, the procedures performed by the host device in FIG. 26 may be handled by using a cloud (or computer resources on a wide-area network) rather than an information terminal such as a smartphone carried by the user (same as described above). In the case where the stickable device 100 that has notified that it had peeled off from the user's body or was just about to peel off is associated (paired) with the another stickable device 100, the cloud not only handles the disconnection from the stickable device 100 that has sent a notice and the cancellation of the authenticated state but also cancels the pairing.

D. Stickable Device with an Imaging Function

The stickable device 100 can include an imaging sensor in the sensor section 710. As illustrated in FIG. 2, the stickable device 100 stuck under the user's eye can capture an image covering a field of view that approximately matches that of a user's viewpoint. Depending on an imaging optics, the stickable device 100 can capture an image covering a wider field of view than that of the user's viewpoint. Also, when installed under the left and right eyes, the stickable devices 100, each having an imaging sensor, can form a stereo camera.

Figure 27:
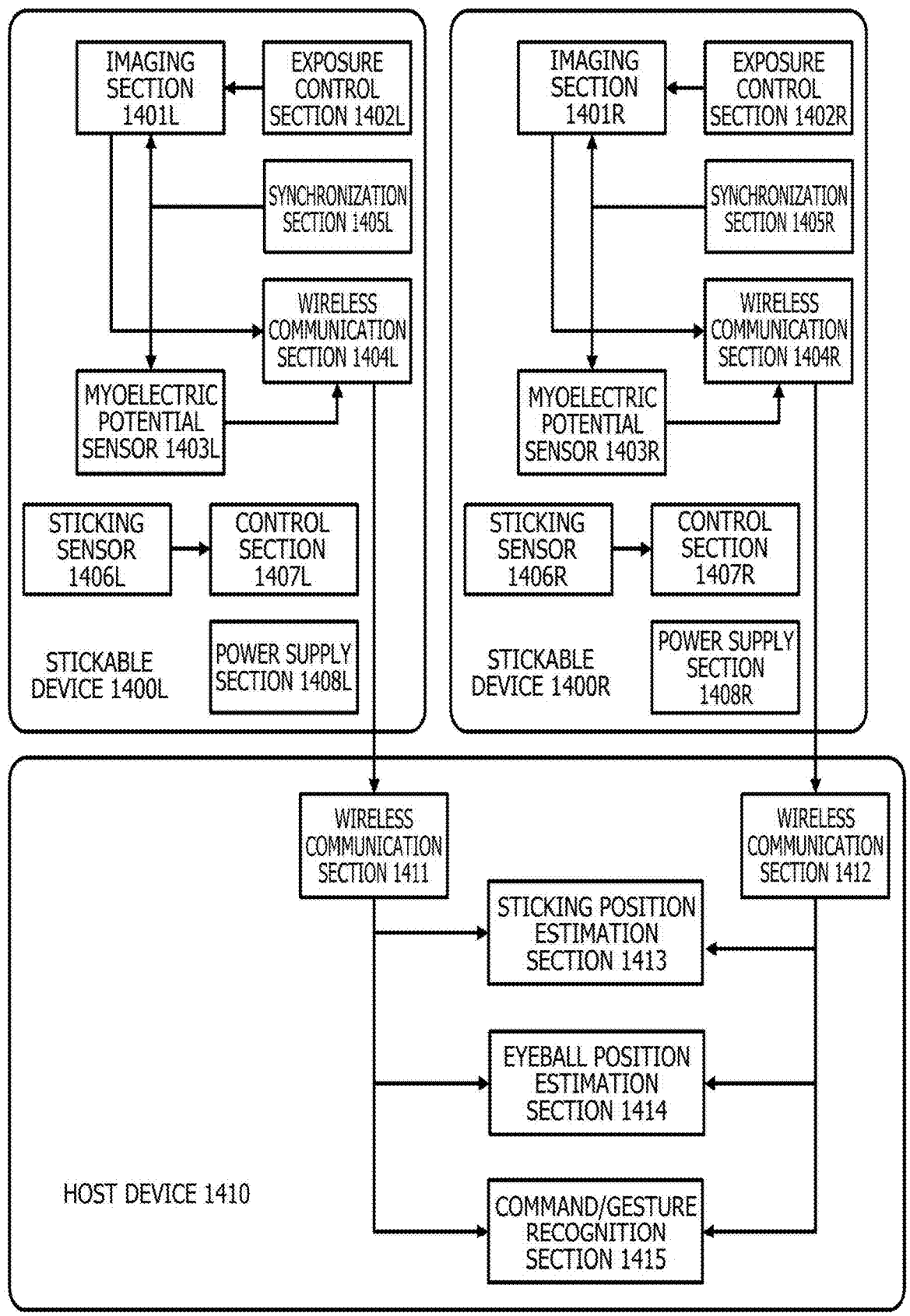
FIG. 27 is a diagram illustrating an example of a system configuration of a stereo camera that includes stickable devices stuck under the user's left and right eyes.

FIG. 27 illustrates an example of a system configuration of a stereo camera realized by a stickable device 1400L stuck under the user's left eye, a stickable device 1400R stuck under the user's right eye, and a host device 1410 that pairs the stickable devices 1400L and 100R. A description will be given below of each section. It should be noted, however, that the stickable devices 1400L and 1400R have approximately the same configuration. Therefore, these devices will be described together as one stickable device.

The one stickable device 1400 includes an imaging section 1401, an exposure control section 1402, a myoelectric potential measurement section 1403, a wireless communication section 1404, a synchronization section 1405, a sticking sensor 1406, a control section 1407, and a power supply section 1408. Although the stickable device 1400 includes other components that are not depicted such as other sensors, these components are omitted for simplification of the drawing.

The sticking sensor 1406 detects the state of sticking between the stickable device 1400 and the user's body (under the eye, here). Details of the method of detecting the sticking state are as described already. The control section 1407 controls the operation of the stickable device 1400 in question on the basis of detection results of the sticking sensor 1406 regarding the sticking state. For example, when the sticking sensor 1406 detects the sticking to the user's body, the control section 1407 sends equipment information and user's biological information to the host device 1410 to proceed with the procedures for initiating the use and pairing. Also, when the sticking sensor 1406 detects the unsticking (the fact that the main body of the stickable device 1400 has peeled off from the user's body or is just about to peel off from the user's body), the control section 1407 proceeds with the procedures for terminating the use such as initializing or deleting internal information and notifying the host device 1410. Also, the power supply section 1408 is maintained in a non-conductive state when the sticking surface of the stickable device 1400 is protected with release paper. When the release paper is peeled off, the power supply section 1408 is set to a conductive state, thus initiating supply of power to each section.

The imaging section 1401 includes, for example, an imaging sensor such as a CMOS (Complementary Metal Oxide Semiconductor). When the stickable device 100 is stuck under the user's eye, the imaging sensor is arranged in such a manner as to be able to capture an image covering a field of view that approximately matches that of the user's viewpoint. The exposure control section 1402 automatically controls the exposure at the time of image capture by the imaging section 1401.

A spherical lens may be used to provide a wider viewing angle of the imaging section 1401. It should be noted, however, that a glass lens is heavy, and a plastic lens tends to increase in size because of its low refractive index. If the lens size or weight increases, there is a possibility that the stickable device 1400 may bend or warp at the time of being stuck. Further, there is a concern that the stickable device 1400 may more readily peel off from under the user's eye and fall. For this reason, a plurality of imaging sensors may be arranged adjacent to the imaging section 1401 to put together the images of the respective imaging sensors, thus realizing wide viewing angle imaging without increasing the lens size and weight while at the same time suppressing the impact of warping. By realizing a wide viewing angle of the imaging section 1401, it is also possible to generate a third-party's viewpoint image covering a wide range around the user and an around-view image that gives an impression of looking down on the user from above. Also, it is possible to estimate a user's gazing point by using the imaging section 1401 having a wide viewing angle and capturing an image including user's eyeball positions. It should be noted that further reduction in weight and thickness may be achieved by using lensless cameras as imaging sensors (the technology of the lensless camera is a technology for realizing images and videos through digital processing by projecting a subject's silhouette with transmissive film in place of a lens).

It should be noted that the shape of irregularities under the eye varies from one individual to another. In the case where the sticking surface of the stickable device 1400 is stuck in such a manner as to follow the shape under the user's eye, it is necessary to correct the direction of line of sight between the plurality of imaging sensors. The position of each imaging sensor may be physically adjusted. Alternatively, a correction procedure may be performed on captured images. The correction procedure may be performed within the stickable device 1400 or on the side of the host device 1410 to which video data is sent.

Also, a plurality of imaging sensors covering different ranges of imaging wavelengths and employing different imaging techniques may be used in combination in the imaging section 1401. For example, the imaging section 1401 may include a combination of a thermo camera, a depth camera, a polarization camera, a night vision camera, and so on.

The myoelectric potential measurement section 1403 measures a myoelectric potential under the user's eye and around the user's eyeball. It is possible to measure a state of relaxation of muscles around the eyeball on the basis of myoelectric potential measurement results, and detect user's eyeball positions and a gazing point. The imaging operation of the imaging section 1401 is controlled on the basis of measurement results of the myoelectric potential measurement section 1403. Also, the myoelectric potential measurement section 1403 can measure myoelectric potentials of user's facial muscles such as mimetic muscles. Therefore, it is possible to estimate a user's emotion on the basis of measurement results of myoelectric potentials and transport emotion data to the host device 1410.

The control section 1407 wirelessly communicates with external equipment outside the stickable device 100. In the example illustrated, wireless signals are transmitted and received between the control section 1407 and the host device 1410. The control section 1407 sends video data captured by the imaging section 1401 to the host device 1410.

Provided, respectively, under the user's left and right eyes, the stickable devices 1400L and 1400R can capture videos that are extremely close to the user's viewpoint, thus providing a stereo image free from sense of discomfort.

It should be noted, however, that pieces of video data captured by each of the left and right imaging sections 1401L and 1401R need to be in synchronism with each other in order for the stickable devices 1400L and 1400R to be used as a stereo camera. Therefore, it is assumed that respective synchronization sections 1405L and 1405R achieve synchronization of the left and right pieces of video data at the time of wireless transmission. For example, one of the synchronization sections 1405L and 1405R plays the role of a master, and the other plays the role of a slave, thus handling the synchronization procedure. Any means may be used to perform the synchronization procedure. For example, the synchronization sections 1405L and 1405R may establish synchronization through direct communication such as proximity communication or adjust synchronization via the host device 1410. By achieving synchronization, it is possible to share the same synchronizing signal between the two stickable devices 1400L and 1400R stuck under the user's left and right eyes. A synchronizing signal acquired between the synchronization sections 1405L and 1405R is assigned at the time of transmission of video data to external equipment.

Also, the wireless communication section 1407 sends, to the host device 1410, measurement results of the myoelectric potential measurement section 1403 and sensor data detected by another sensor (not depicted in FIG. 27). For example, a user's biological signal acquired by the biological sensor can be used as an index of video data. A synchronizing signal acquired between the synchronization sections 1405L and 1405R is assigned at the time of transmission of a biological signal to external equipment.

The host device 1410 includes, for example, an information terminal such as a smartphone carried by the user. It should be noted, however, that FIG. 27 restrictively illustrates only those functional components specialized in paired operation with the stickable device 1400. The host device 1410 may include other functional components that are not depicted. It should be noted, however, that the functions of the host device 1410 can be provided on the cloud.

The host device 1410 includes a first wireless communication section 1411, a second wireless communication section 1412, a sticking position estimation section 1413, an eyeball position estimation section 1414, and a command/gesture recognition section 1415.

The first wireless communication section 1411 and the second wireless communication section 1412 engage in wireless communication with the stickable device 1400L stuck under the user's left eye and the stickable device 1400R stuck under the user's right eye, respectively. The first wireless communication section 1411 and the second wireless communication section 1412 may include a single wireless communication circuit so as to alternately wirelessly communicate with the stickable devices 1400L and 1400R in a time-shared manner.

The first wireless communication section 1411 and the second wireless communication section 1412 receive, together with video data, myoelectric potential measurement results, emotion data based on myoelectric potential, a biological signal detected by the biological sensor, sensor data detected by other sensors, or the like from the stickable device 1400L and the stickable device 1400R stuck under the right eye, respectively.

The sticking position estimation section 1413 estimates the sticking position of each of the stickable device 1400L stuck under the left eye and the stickable device 1400R stuck under the right eye. There is a possibility that the stickable devices 1400L and 1400R may vary in sticking position. In the case where the stickable devices 1400L and 1400R are used as a stereo camera, the variation in sticking position affects misalignment in a viewing angle and a center position between left and right pieces of captured image data. For this reason, the sticking position estimation section 1413 estimates the sticking positions of the stickable devices 1400L and 1400R from the captured image data received from each of the stickable devices 1400L and 1400R. Then, in the case where the sticking positions are out of alignment, image correction is performed to ensure that the viewing angle and the center position of one piece of the captured image data match those of the other piece of the captured image data.

The eyeball position estimation section 1414 estimates user's left and right eyeball positions on the basis of myoelectric potential data around the user's eyeballs received from each of the stickable devices 1400L and 1400R, and detects the gazing point of the user under whose left and right eyes the stickable devices 1400L and 1400R are stuck, respectively.

Although not depicted in FIG. 27, the host device 1410 may include a video recording section that records video data received from each of the stickable devices 1400L and 1400R. At the time of recording, video data may be recorded in association with the user's gazing point detected by the eyeball position estimation section 1414.

The command/gesture recognition section 1415 recognizes a command that the user intends to give or a gesture that the user intends to make on the basis of user's left and right eyeball positions detected by the eyeball position estimation section 1414 and the user's motion included in the video data received from each of the stickable devices 1400L and 1400R. Also, the command/gesture recognition section 1415 recognizes a command that the user intends to give on the basis of user's emotion data sent from each of the stickable devices 1400L and 1400R.

The host device 1410 controls its own operation in response to the command or gesture recognized and further wirelessly sends operating instructions to each of the stickable devices 1400L and 1400R. Also, the host device 1410 can control reproduction output (e.g., starting reproduction, stopping reproduction, pausing, fast-forwarding, rewinding, moving viewpoint) of the video data received from each of the stickable devices 1400L and 1400R and can edit the video data in response to the command or gesture recognized. For example, it is possible to index video data by using user's biological signals acquired by the biological sensor of each of the stickable devices 1400L and 1400R.

The operation sequence of the system illustrated in FIG. 27 is as follows.

(1) First, the first stickable device 1400 and the host device 1410 are paired. The host device 1410 may read, for example, an NFC or a QR code to achieve direct pairing with the stickable device 1400. Alternatively, information regarding pairing may be remotely written to a eSIM each incorporated in the stickable device 1400 and the host device 1410 for pairing.

(2) Next, the user peels off the release paper from the sticking surface of the first stickable device 1400. This initiates supply of power from the power supply section 1408 to each section. Further, a sleep state of the stickable device 1400 is cancelled by sticking the stickable device 1400 to a given location of the user's body (under the eye, here).

(3) When a user's biological signal is acquired by using a biological sensor (not depicted in FIG. 27), the stickable device 1400 sends a feature quantity of the biological signal to the host device 1410 on the basis of equipment information of the stickable device 1400 and the feature quantity of the biological signal. The host device 1410 carries out an equipment authentication of the stickable device 1400 and a user authentication. If these authentications succeed, the connection between the first stickable device 1400 and the host device 1410 is complete. The above description and FIG. 25 should be referred to for details of the authentication procedure.

(4) Then, the procedures described above in steps (1) to (3) are performed for the second stickable device 1400, thus completing the connection with the host device 1410 by way of paring with the host device 1410, sticking to the user's body (under the user's other eye), and proceeding with the authentication procedure. It should be noted that either the stickable device 1400L or 1400R can be selected as the first stickable device (that is, either the stickable device 1400L or 1400R can be connected first). Also, in the case where three or more stickable devices 1400 are connected to the host device 1410, the procedures described above in steps (1) to (3) are repeated similarly for the third and subsequent stickable devices 1400.

(5) The respective stickable devices 1400L and 1400R achieve synchronization by using the synchronization sections 1405L and 1405R thereof, respectively, to ensure synchronization of the video data wirelessly sent to the host device 1410. For example, the synchronization sections 1405L and 1405R may establish synchronization through direct communication such as proximity communication or adjust synchronization by way of the host device 1410.

(6) Next, the sticking position estimation section 1413 on the side of the host device 1410 estimates the sticking positions of the stickable devices 1400L and 1400R from captured image data received from each of the stickable devices 1400L and 1400R. Then, in the case where the sticking positions are out of alignment, setup is performed for image correction to ensure that the viewing angle and the center position of one piece of the captured image data match those of the other piece of the captured image data. The variation in sticking position of the stickable devices 1400L and 1400R affects misalignment in the viewing angle and the center position between left and right pieces of captured image data.

(7) After the completion of the pairing between each of the stickable devices 1400L and 1400R and the host device 1410, the authentication, and the connection, and further the synchronization procedure between the stickable devices 1400L and 1400R and the sticking position correction as described above, the wireless transport of video data from each of the stickable devices 1400L and 1400R to the host device 1410 is initiated. The same synchronizing signal is assigned to the video data. Also, sensor data detected by the sensor of each of the stickable devices 1400L and 1400R is wirelessly transmitted to the host device 1410 together with the video data.

(8) The host device 1410 sends the video data and the sensor data received from each of the stickable devices 1400L and 1400R further to a remote device.

(9) The remote device reproduces and outputs the video data received by way of the host device 1410. Also, the remote device may give, to a remote user using the remote device, a sensory feedback using five senses other than vision on the basis of the sensor data received.

The term "remote device" here refers, for example, to a head-mounted display or other forms of display apparatus capable of reproducing and outputting a VR (Virtual Reality) video or an AR (Augmented Reality) video.

Figure 28:
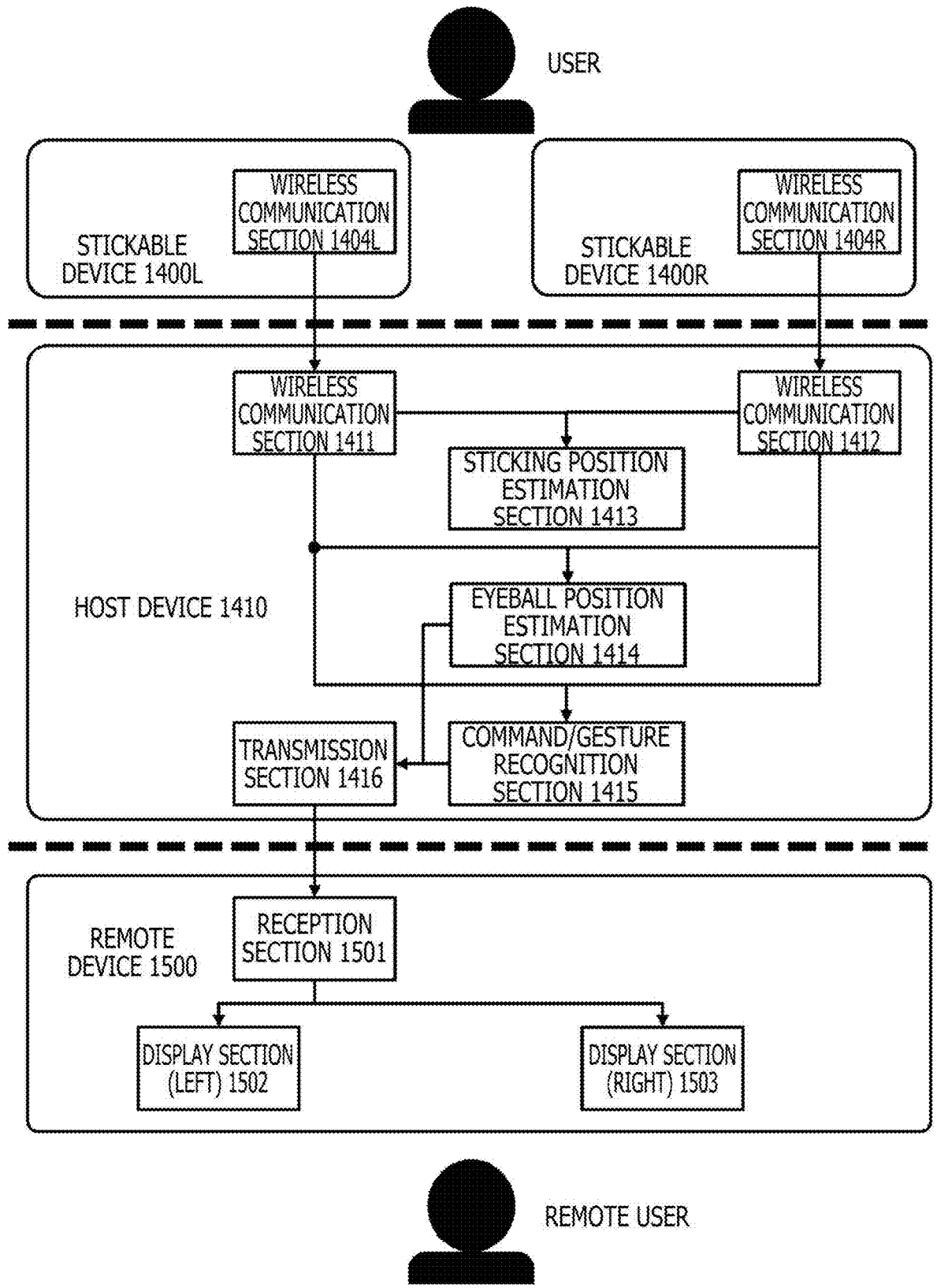
FIG. 28 is a diagram illustrating a configuration example of a video transport system of a stereo camera.

FIG. 28 is a diagram illustrating a configuration example of a video transport system of a stereo camera that includes the left and right stickable devices 1400L and 1400R, the host device 1410, and further a remote device 1500. It should be noted that the configurations of the stickable devices 1400L and 1400R and the host device 1410 are similar to those illustrated in FIG. 27, and some components are omitted for simplification of the drawing in FIG. 28.

The host device 1410 further includes a transmission section 1416 to transport information to the remote device. Not only video data and sensor data received from each of the stickable devices 1400L and 1400R but also estimation results of the user's eyeball positions and command and gesture recognition results are sent from the transmission section 1416.

The means of communication between the host device 1410 and the remote device 1500 is not particularly limited. For example, communication using a wireless or wired LAN (Local Area Network) or a home network may be used. Alternatively, communication using a wide area network such as the Internet may be used.

The remote device 1500 includes a reception section 1501 and left and right display sections 1502 and 1503. The reception section 1501 receives information from the host device 1410. Basically, video data captured by the stickable device 1400L stuck under the user's left eye is displayed on the left display section 1502, and video data captured by the stickable device 1400R stuck under the user's right eye is displayed on the right display section 1503, thus presenting a stereo video to the remote user. It is assumed that the left and right display sections 1502 and 1503 display a video by achieving synchronization on the basis of the synchronizing signal assigned to the received video data. It should be noted, however, that the remote device 1500 may be operated as a mono camera that displays only the video data of only one of the left and right stickable devices 1400L and 1400R.

Also, the remote device 1500 may further include an actuator (not depicted) that drives on the basis of the sensor data received by way of the host device 1410, and that gives, to the remote user, a sensory feedback using five senses other than vision.

In a video transport system as illustrated in FIG. 28, the stickable devices 1400L and 1400R are assumably stuck under the user's left and right eyes, respectively, tracking the user's head motion and capturing images of a surrounding situation. However, the practical viewing angle of the user depends on not only the head motion but also the eyeballs' direction. For this reason, even though video data captured by the stickable devices 1400L and 1400R on the side of the remote device 1500 is presented, a video matching the user's viewing angle may not be presented to the remote user.

For this reason, a video matching the user's viewing angle may be presented to the remote user by detecting the user's left and right orbicularis oculi muscles and controlling, on the basis of detection results, the left and right orbicularis oculi muscles of the remote user.

Figure 29:
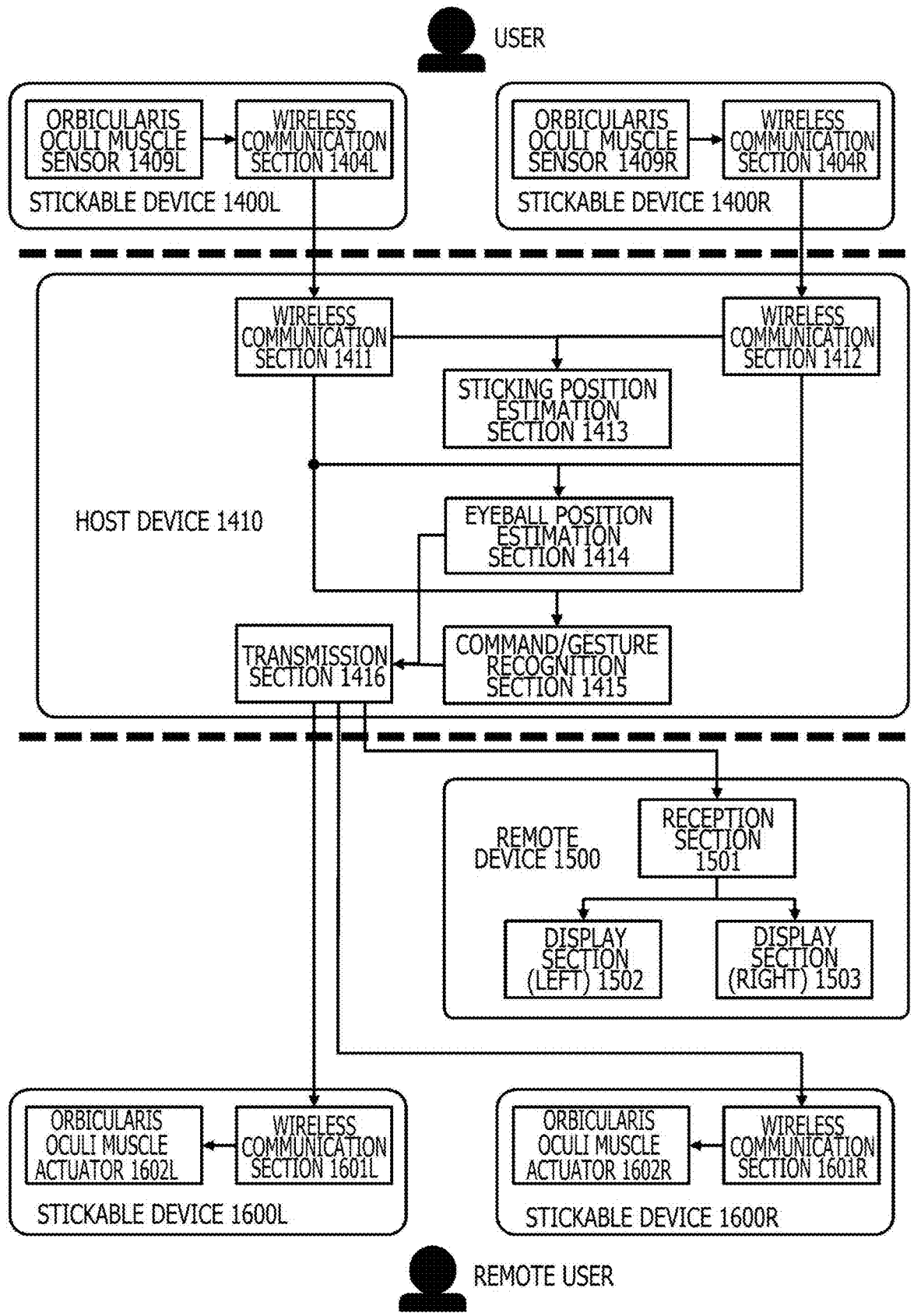
FIG. 29 is a diagram illustrating a configuration example of a video transport system of a stereo camera including orbicularis oculi muscle control.

FIG. 29 illustrates a configuration example of a video transport system of a stereo camera including orbicularis oculi muscle control.

The stickable devices 1400L and 1400R stuck under the user's left and right eyes differ from those in FIGS. 27 and 28 in that orbicularis oculi muscle sensors 1409L and 1409R are further included. Each of the orbicularis oculi muscle sensors 1409L and 1409R detects the orbicularis oculi muscle as one of the first sensor sections 711. The respective stickable devices 1400L and 1400R send orbicularis oculi muscle data detected by the orbicularis oculi muscle sensors 1409L and 1409R from wireless communication sections 1404L and 1404R together with video data, a biological signal, other sensor data, and so on. It is assumed that a synchronizing signal is assigned to sensor data wirelessly sent from each of the stickable devices 1400L and 1400R.

On the other hand, the system configuration differs from that illustrated in FIG. 28 in that stickable devices 1600L and 1600R are stuck around the remote user's left and right eyes (e.g., under the eyes), respectively.

The stickable devices 1600L and 1600R are mainly characterized in including orbicularis oculi muscle actuators 1602L and 1602R, respectively, as one of the first actuator sections 721. The orbicularis oculi muscle actuators 1602L and 1602R drive the orbicularis oculi muscles of the remote user.

The stickable devices 1600L and 1600R receive orbicularis oculi muscle data, detected by the orbicularis oculi muscle sensors 1409L and 1409R in the stickable devices 1400L and 1400R, by using wireless communication sections 1601L and 1601R by way of the host device 1410. Then, each of the orbicularis oculi muscle actuators 1602L and 1602R is driven on the basis of the orbicularis oculi muscle data received, thus controlling the left and right orbicularis oculi muscles of the remote user and presenting, on the remote device 1410, a video matching the user's viewing angle.

E. Stickable Device with an Odor Suppression Function

Giving a stimulus to the user's olfactory perception by providing a pleasant scent or the like produces aromatherapy-like effects such as allowing the user to refresh his or her mind, relax, and get into a better physical condition. Also, there is a possibility that body odor may give a sense of discomfort to surrounding people or the user himself or herself. For this reason, a stickable device stuck to the user's torso or the like may include an odor suppression section as one of the first sensor sections 711 or one of the second sensor sections 712. The odor suppression section has at least one of a fragrancing function or a deodorizing function. The control section need only control driving of fragrancing or deodorizing by the odor suppression section on the basis of the odor data collected by the odor sensor. For example, the stickable device may be controlled remotely from the host device or a cloud in such a manner as to achieve fragrancing suitable for time, place, and occasion on the basis of context such as a user's activity schedule, positional information, and surrounding environment.

Figure 30:
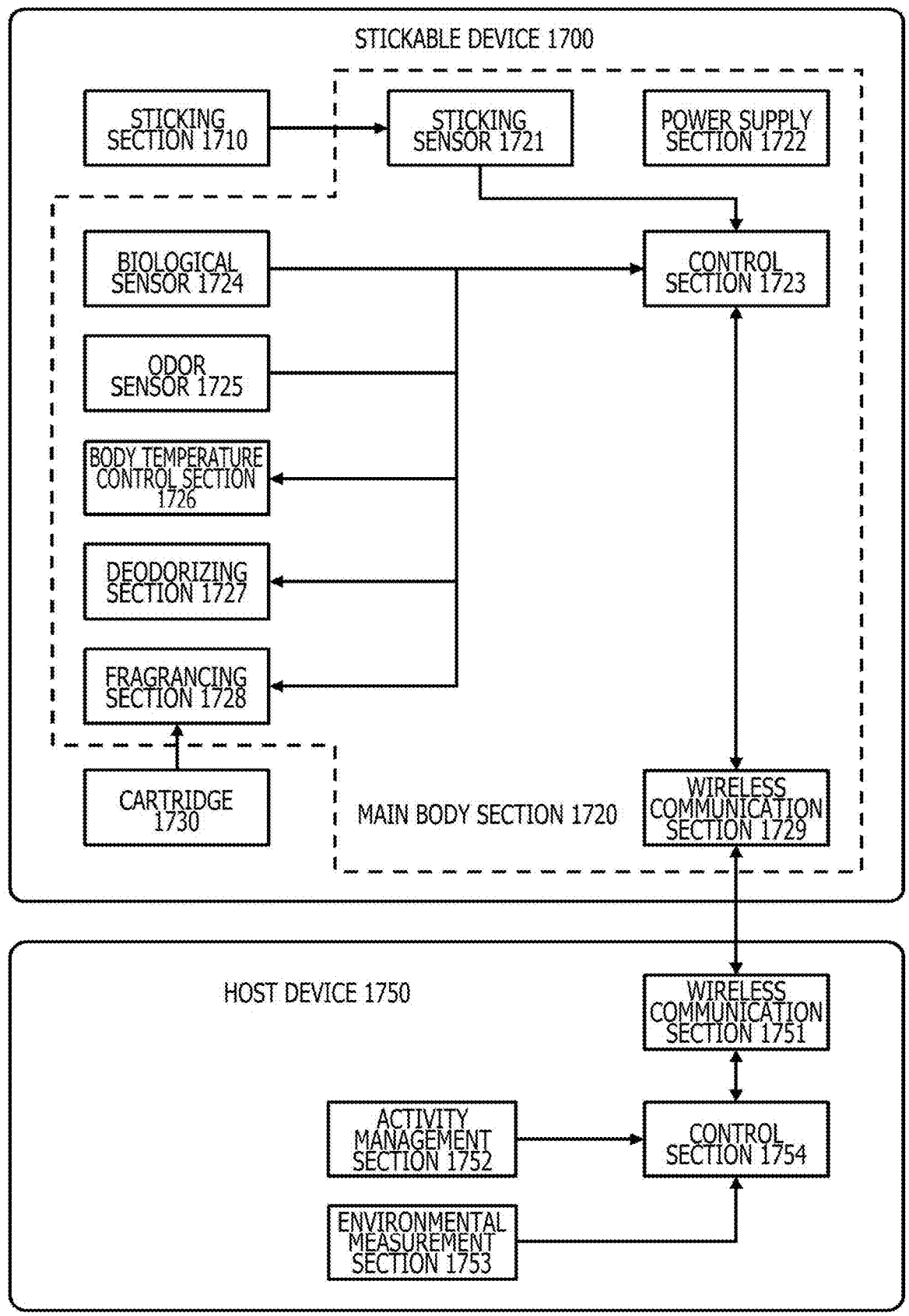
FIG. 30 is a diagram illustrating examples of functional configurations of a stickable device 1700 with an odor suppression function and a host device 1750 that coordinates with the stickable device 1700.

FIG. 30 illustrates examples of functional configurations of a stickable device 1700 with an odor suppression function and a host device 1750 that coordinates with the stickable device 1700.

Figure 31:
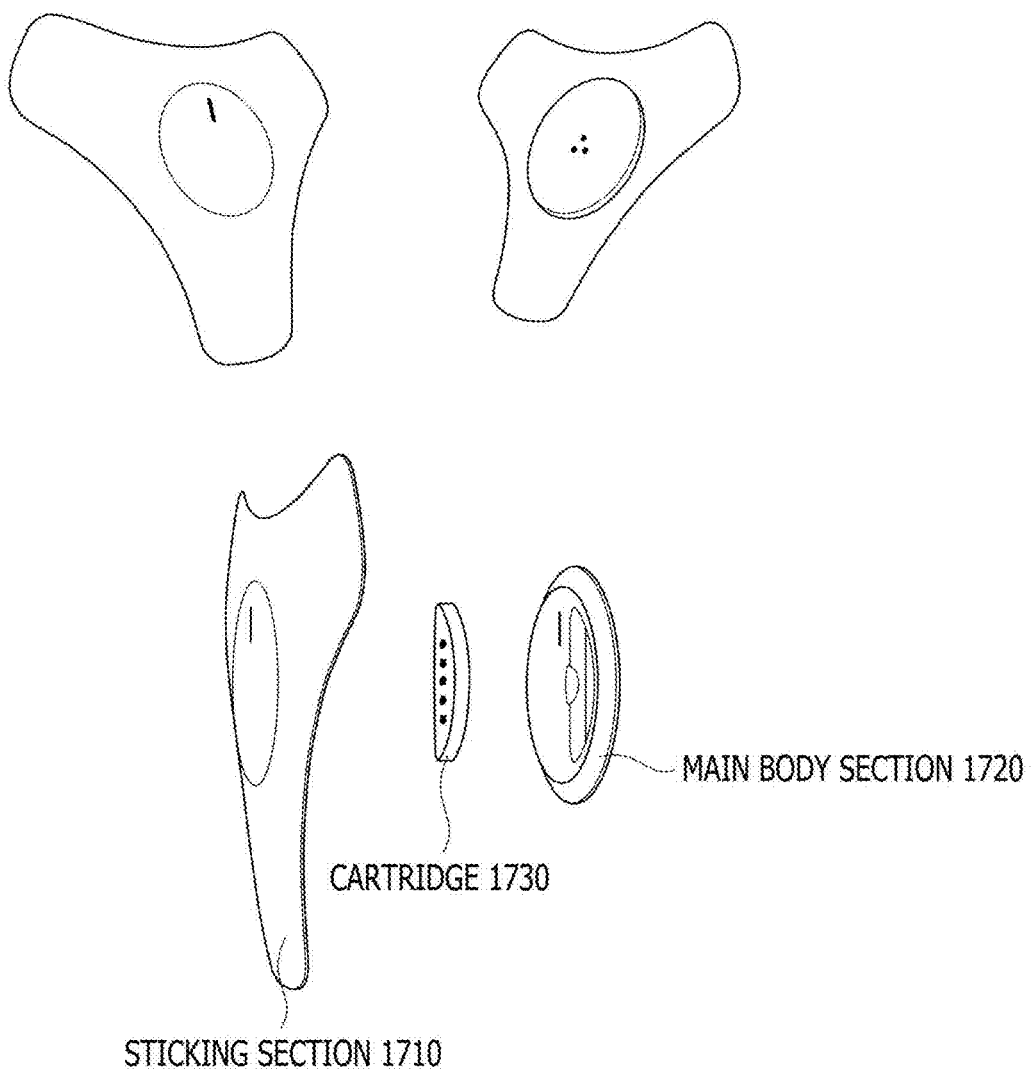
FIG. 31 is a diagram illustrating a manner in which the stickable device 1700 is decomposed into a sticking section 1710, a main body section 1720, and a cartridge 1730.

The stickable device 1700 includes a sticking section 1710, a main body section 1720, and a cartridge 1730. FIG. 31 illustrates a manner in which the stickable device 1700 (refer, for example, to FIG. 10 and FIGS. 11 to 17) stuck to an upper center portion of the user's back is decomposed into the sticking section 1710, the main body section 1720, and the cartridge 1730.

The sticking section 1710 has a sticking surface (or adhesive surface) that comes in contact with the user's body surface such as the back. Also, the sticking section 1710 covers an upper surface of the main body section 1720. Conversely speaking, the upper surface of the main body section 1720 is exposed when the sticking section 1710 is peeled off. Also, the main body section 1720 includes several circuit components (described later) and a pocket for accommodating the cartridge 1730.

As is clear from FIG. 31, the main body section 1720 is fastened to the user's body by attaching the cartridge 1730 to the pocket of the main body section 1720, covering the upper surface of the main body section 1720 with the sticking section 1710, and sticking the sticking section 1710 to a given location of the user's body, thus bringing the stickable device 1700 into a ready-to-use state.

A fragrance agent is stored in the cartridge 1730. Driving the actuator (fragrancing section 1728 described later) in the main body section 1720 causes a fragrance agent in the cartridge 1730 to be sprayed, thus releasing an aroma. A plurality of types of fragrance agents may be stored in the cartridge 1730, thus allowing one of the fragrance agents to be selected or two or more fragrance agents to be mixed for use.

The cartridge 1730 is consumable and needs to be replaceable with the new cartridge 1730 when the cartridge 1730 runs out of the fragrance agent. Also, it is possible to change the aroma released by having the plurality of types of cartridges 1730 having different aromas, and replacing the cartridge 1730 attached to the pocket of the main body section 1720 with a different type.

In order to replace the cartridge 1730, the sticking section 1710 covering the upper surface of the main body section 1720 should preferably be removable. Also, the sticking section 1710 comes in contact with the user's body surface. Therefore, the sticking section 1710 should preferably be suited to being cleaned and not lead to deterioration of the adhesive capability of the adhesive surface even when cleaned.

The main body section 1720 includes a sticking sensor 1721, a power supply section 1722, a control section 1723, a biological sensor 1724, an odor sensor 1725, a body temperature control section 1726, a deodorizing section 1727, a fragrancing section 1728, and a wireless communication section 1729.

The sticking sensor 1721 detects the state of sticking between the sticking section 1710 (in other words, the stickable device 1700) and the user's body. Details of the method of detecting the sticking state are as described already. The control section 1723 controls the operation of the stickable device 1700 on the basis of detection results of the sticking state detected by the sticking sensor 1721. For example, when the sticking sensor 1721 detects the sticking to the user's body, the control section 1723 sends equipment information and a user's biological signal to the host device 1750 to proceed with the procedures for initiating the use and pairing. Also, when the sticking sensor 1721 detects the unsticking (the fact that the main body of the stickable device 1700 has peeled off from the user's body or is just about to peel off from the user's body), the control section 1723 proceeds with the procedures for terminating the use such as initializing or deleting internal information and notifying the host device 1750. Also, for example, the power supply section 1723 is maintained in a non-conductive state when the sticking surface of the sticking section 1710 is protected with release paper. For example, when the release paper is peeled off, the power supply section 1723 is set to a conductive state, thus initiating supply of power to each section.

When the stickable device 1700 is stuck to the user's body, the stickable device 1700 and the host device 1750 perform, for example, given equipment authentication and user authentication processes in accordance with the processing sequence illustrated in FIG. 25 to establish connection. Also, when the fact that the stickable device 1700 has peeled off from the user's body or is just about to peel off from the user's body (i.e., unsticking) is detected, the stickable device 1700 initializes or deletes at least part of the information stored therein and further notifies the unsticking to the host device 1750 in accordance with the processing sequence illustrated in FIG. 26 to proceed with disconnection and other procedures.

The biological sensor 1724 acquires biological information such as body temperature, heartbeat, presence or absence of perspiration, sweat components, or the like of the user to whom the stickable device 1700 in question is stuck. The biological sensor 1724 can be said to be one of the first sensor sections 711 that detects the user (human body) information. Also, the odor sensor 1725 detects an odor of the stickable device 1700 in question or the user's surroundings. Also, the stickable device 1700 may be equipped with sensors other than those illustrated in FIG. 30.

The body temperature control section 1726 temporarily controls the user's body temperature primarily by heating or cooling the portion of the stickable device 1700 in contact with the user's body surface. The body temperature control section 1726 includes, for example, a Peltier element. The body temperature control section 1726 can be said to be one of the first actuator sections 721 that output information to the user (human body).

The deodorizing section 1727 physically eliminates a component that causes an odor in the surroundings of the stickable device 1700 in question (e.g., user's body odor) or chemically transforms such a component into an odorless component. For example, the deodorizing section 1727 may include Triporous (registered trademark), a new plant-derived porous carbon material. It should be noted that Triporous is a porous carbon material having a fine structure and adsorption properties and includes surplus biomass (reusable animal-derived organic resource) such as rice husks that include silicon compounds. Triporous is disclosed, for example, in PTL 5. The content disclosed in PTL 5 is incorporated in the present application specification.

The fragrancing section 1728 stirs the fragrance agent inside the cartridge 1730, thus spraying the agent and releasing an aroma. For example, AROMASTICK, which is a cartridge type aroma provision apparatus, is known and disclosed, for example, in PTL 6. The content disclosed in PTL 6 is incorporated in the present application specification.

The deodorizing section 1727 and the fragrancing section 1728 can be said to be the second actuator sections 722 that output information outside the user (to the outside world and surrounding people).

The control section 1723 controls the driving of the actuators such as the body temperature control section 1726, the deodorizing section 1727, and the fragrancing section 1728, for example, on the basis of user's biological information detected by the biological sensor 1724 and sensor data detected by other sensors.

For example, when recognizing a user's poor physical condition on the basis of the user's body temperature, change in heartbeat, sweat components, and so on, the control section 1723 makes an attempt to improve the user's physical condition, for example, by instructing the body temperature control section 1726 to keep the user warm or instructing the fragrancing section 1728 to perform fragrancing. Also, when recognizing that the user is feeling hot on the basis of the user's body temperature increase or perspiration, the control section 1723 attempts to make the user feel comfortable, for example, by instructing the body temperature control section 1726 to cool the user. Also, when detecting the user's body odor or an abnormal odor in the surroundings with the odor sensor 1725, the control section 1723 attempts to make the user's working environment comfortable, for example, by instructing the deodorizing section 1727 to perform deodorizing or instructing the fragrancing section 1728 to perform fragrancing. In the case where a plurality of types of fragrance agents is stored in the single cartridge 1730, the control section 1723 may control the selection of a fragrance agent used by the fragrancing section 1728 in accordance with context such as user's physical condition and body order or a user's activity schedule and surrounding environment.

The wireless communication section 1729 wirelessly communicates with external equipment such as the host device 1750. The control section 1723 may send user's biological information detected by the biological sensor 1724 and sensor data detected by other sensors to the host device 1750 via the wireless communication section 1729. Also, the control section 1723 may control the driving of the actuators such as the body temperature control section 1726, the deodorizing section 1727, and the fragrancing section 1728 on the basis of information (e.g., command) received from the host device 1750.

The host device 1750 includes an information terminal such as a smartphone carried by the user. In the example illustrated in FIG. 30, the host device 1750 includes a wireless communication section 1751, an activity management section 1752, an environmental measurement section 1753, and a control section 1754.

The wireless communication section 1751 wirelessly communicates with the wireless communication section 1729 on the side of the stickable device 1700. The activity management section 1752 manages an activity schedule of the user to whom the stickable device 1700 is stuck. For example, it is possible to acquire information regarding the user's activity schedule, for example, on the basis of data used by an application such as schedule book that runs on a smartphone. Also, the activity management section 1752 manages a scheduler that instructs the stickable device 1700 to drive the body temperature control section 1726, the deodorizing section 1727, and the fragrancing section 1728 on the basis of the user's activity schedule. Also, the environmental measurement section 1753 measures data regarding the user's surrounding environment such as outside temperature.

The control section 1754 sends, to the stickable device 1700 via the wireless communication section 1751, the user's activity schedule managed by the activity management section 1752 and environmental data such as outside temperature measured by the environmental measurement section 1753. The stickable device 1700 can control the driving of the actuators such as the body temperature control section 1726, the deodorizing section 1727, and the fragrancing section 1728 on the basis of context such as the user's activity schedule and surrounding environment.

Also, the control section 1754 on the side of the host device 1750 may send, to the stickable device 1700 via the wireless communication section 1751, a driving request instructing the driving of these actuators on the side of the stickable device 1700 on the basis of context such as the user's activity schedule and surrounding environment. In the case where a plurality of types of fragrance agents is stored in the single cartridge 1730, the control section 1754 may control the selection of a fragrance agent used by the fragrancing section 1728 in accordance with user's context.

It should be noted that the procedure performed by the host device 1750 in FIG. 30 may be handled by using a cloud (or computer resources on a wide-area network) rather than an information terminal such as a smartphone carried by the user.

FIG. 32 illustrates, in a flowchart form, a processing sequence for the host device 1750 to carry out fragrance control on the side of the stickable device 1700 on the basis of a user's activity schedule. It is assumed, as a precondition for carrying out this processing sequence, that the connection between the stickable device 1700 and the host device 1750 is complete.

On the side of the host device 1750, the activity management section 1752 analyzes the activity schedule of the user to whom the stickable device 1700 is stuck (step S1911), and the control section 1754 estimates whether a fragrancing request has been made on the basis the analysis results (step S1912). If no fragrancing request has been made (No in step S1912), the procedure remains on standby for a certain amount of time (step S1913) and then returns to step S1911. Also, in the case where it is decided on the basis of the user's activity schedule that a fragrancing request has been made (Yes in step S1912), the control section 1754 notifies a fragrancing request to the stickable device 1700 via the wireless communication section 1751 (step S1914).

On the side of the stickable device 1700, on the other hand, the control section 1723 checks, every certain amount of time (step S1901), whether a fragrancing request has been received from the host device 1750 (step S1902).

Then, when the wireless communication section 1728 receives a fragrancing request from the host device 1750 (Yes in step S1902), the control section 1723 specifies a direction to the fragrancing section 1728. In response, the fragrancing section 1728 selects the fragrance agent specified in the fragrancing request from the single cartridge 1730 (step S1903) and sprays the fragrance agent (step S1904).

The stickable device 1700 can spray a fragrance agent in accordance with the user's activity schedule managed on the side of the host device 1750 by following the processing sequence illustrated in FIG. 32. For example, the stickable device 1700 can spray a fragrance agent that provides a sense of exhilaration to suppress drowsiness in the afternoon after lunch and a mind-easing fragrance agent to relax the user at an estimated closing time of the day's work.

It should be noted that the procedure performed by the host device 1750 in FIG. 32 may be handled by using a cloud (or computer resources on a wide-area network) rather than an information terminal such as a smartphone carried by the user.

Also, the stickable device 1700 can autonomously perform fragrancing on the basis of biological information detected by the biological sensor 1723 irrespective of whether the host device 1750 makes a request. In such a case, the host device 1750 may adjust a schedule for making a fragrancing request to the stickable device 1700 in accordance with circumstances in which fragrancing is performed by the stickable device 1700.

FIG. 33 illustrates, in a flowchart form, a processing sequence for the host device 1750 to adjust a schedule for making a fragrancing request on the basis of a history of performing fragrancing on the side of the stickable device 1700. It is assumed, as a precondition for carrying out this processing sequence, that the connection between the stickable device 1700 and the host device 1750 is complete.

On the side of the stickable device 1700, the control section 1723 checks, every certain amount of time (step S2001), sensor data detected by the biological sensor 1724 and the odor sensor 1725 to confirm whether there is any user's odor or odor in the surroundings beyond a prescribed level or whether there is any anomalous user's biological information such as user's body temperature beyond a prescribed level or any anomaly in the surrounding environment (step S2002).

When an odor beyond a prescribed level or a user's body temperature beyond a prescribed level is detected (Yes in step S2002), the control section 1723 instructs the deodorizing section 1727 to deodorize the user's body odor or the odor in the surroundings, instructs the fragrancing section 1728 to perform fragrancing, or instructs the body temperature control section 1726 to cool or heat the user's body. In response, deodorizing by the deodorizing section 1727, fragrancing by the fragrancing section 1728, or cooling or heating of the user's body by the body temperature control section 1726 is performed (step S2003).

For example, when detecting the rise in user's body temperature because of the excitement felt by the user, the control section 1723 drives the body temperature control section 1726 to cool the user's body, temporarily lowering the body temperature. Alternatively, when detecting that the user is feeling cold or chills, the control section 1723 drives the body temperature control section 1726 to heat the user's body, temporarily raising the body temperature. Also, when detecting the user's body odor or an odor in the surroundings, the control section 1723 drives the deodorizing section 1727 to perform deodorizing or drives the fragrancing section 1728 to perform fragrancing, thus improving the surrounding environment.

Thereafter, the control section 1723 notifies a history of performing deodorizing by the deodorizing section 1727, fragrancing by the fragrancing section 1728, or cooling or heating of the user's body by the body temperature control section 1726 to the side of the host device 1750 via the wireless communication section 1729 (step S2004).

On the side of the host device 1750, on the other hand, the control section 1754 checks, every certain amount of time (step S2011), whether the performance history has been notified from the stickable device 1700 (step S2012).

Then, when the performance history has been notified from the stickable device 1700 (Yes in step S2012), the control section 1754 analyzes the received performance history (step S2013) and adds or changes events for instructing deodorizing, fragrancing, cooling or heating of the user's body, and so on in the scheduler that instructs the driving of the body temperature control section 1726, the deodorizing section 1727, and the fragrancing section 1728 on the side of the stickable device 1700 (step S2014).

As described above, the stickable device 1700 notifies a performance history of driving the actuators including deodorizing, fragrancing, and body temperature control to the host device 1750, thus allowing the side of the host device 1750 to add or change events in the scheduler that instructs the driving of the actuators for deodorizing, fragrancing, and body temperature control on the basis of analysis results of the performance history. This makes it possible for the stickable device 1700 to perform, from here onward, deodorizing, fragrancing, or body temperature control proactively under the instruction from the host device 1750, thus dealing with anomalies found in the user's biological information and the surrounding environment.

It should be noted that the procedure performed by the host device 1750 in FIG. 33 may be handled by using a cloud (or computer resources on a wide-area network) rather than an information terminal such as a smartphone carried by the user.

INDUSTRIAL APPLICABILITY

A detailed description has been given of the technology disclosed in the present specification with reference to a specific embodiment. However, it is obvious that a person skilled in the art can modify or replace the embodiment in question without departing from the gist of the technology disclosed in the present specification.

The information processing apparatus disclosed in the present specification is a wearable device stuck to a body surface (skin) for use and is stuck, for example, to locations of the user's body such as the temple, middle of the forehead, back of the ear, under the chin, the neck, base of the neck, the throat, upper arm, the forearm, the wrist, back of the hand, and the abdomen for use.

Also, a similar stickable information processing apparatus can be stuck not only to a human body but also to various animals (e.g., pet animals, livestock, working animals), plants (including plants grown as edible plants or house plants, and wild plants), and machines such as mobile objects for use as an IoT device.

In short, the technology disclosed in the present specification has been described by way of illustration, and the content described in the present specification should not be interpreted restrictively. The claims should be taken into consideration to decide the gist of the technology disclosed in the present specification.

It should be noted that the technology disclosed in the present specification can also have the following configurations.

(1)

An information processing apparatus including:

a sensor;

a communication section adapted to wirelessly communicate with external equipment;

a control section adapted to control the sensor and the communication section;

a power supply section adapted to supply power to at least one of the sensor, the communication section, or the control section;

a housing section adapted to accommodate at least one of the sensor, the communication section, the control section, or the power supply section;

a sticking section adapted to fasten the housing section to a user; and a sticking sensor adapted to detect a state of sticking between the user and the housing on the sticking section, in which the control section controls communication operation of the communication section in response to the sticking state detected by the sticking sensor.

(2)

The information processing apparatus of feature (1), in which the control section performs control such that a given signal is wirelessly sent to external equipment via the communication section in response to detection, by the sticking sensor, of a fact that the sticking section has peeled off from the user or is just about to peel off from the user.

(3)

The information processing apparatus of feature (2) further including:

a host device adapted to engage in wireless communication via the communication section.

(4)

The information processing apparatus of feature (3), in which the host device notifies the user in response to reception of the given signal.

(5)

The information processing apparatus of feature (3) or (4) in which the host device is capable of performing an authentication procedure of the user on the basis of sensor data detected by the sensor, and the host device cancels a user authentication established by the authentication procedure as a result of the reception of the given signal.

(6)

The information processing apparatus of any one of features (1) to (5) further including:

a storage section adapted to store internal information of the information processing apparatus, in which the control section initializes or deletes given information stored in the storage section in response to detection, by the sticking sensor, of a fact that the sticking section has peeled off from the user or is just about to peel off from the user.

(7)

The information processing apparatus of feature (6), in which the storage section stores equipment information of the information processing apparatus, and the control section initializes or deletes the equipment information stored in the storage section in response to the detection, by the sticking sensor, of the fact that the sticking section has peeled off from the user or is just about to peel off from the user.

(8)

The information processing apparatus of feature (6) or (7), in which the storage section stores sensor data detected by the sensor, and the control section initializes or deletes the sensor data stored in the storage section in response to the detection, by the sticking sensor, of the fact that the sticking section has peeled off from the user or is just about to peel off from the user.

(9)

The information processing apparatus of any one of features (1) to (8), in which a surface of the sticking section is protected with release paper before use of the information processing apparatus, and the information processing apparatus is activated in response to peeling-off of the release paper from the sticking section.

(10)

The information processing apparatus of feature (9), in which the release paper includes a non-conductive section in the shape of a tongue piece that insulates the power supply section, and when the release paper is peeled off from the sticking section, the non-conductive section is detached, bringing the power supply section into a conductive state.

(11)

The information processing apparatus of feature (9), in which the control section activates the information processing apparatus in response to detection, by the sticking sensor, of a fact that the release paper has been peeled off from the sticking section.

(12)

The information processing apparatus of any one of features (1) to (11), in which the sensor includes an imaging sensor having an imaging function, and the housing section is stuck near a user's eyeball to capture an image that corresponds to at least part of a user's field of view by the imaging sensor.

(13)

The information processing apparatus of feature (12), in which the housing section is stuck near one of the user's left and right eyeballs, and the same synchronizing signal shared with the other information processing apparatus stuck near the user's other eyeball is assigned to wirelessly send captured image data captured by the imaging sensor from the communication section.

(14)

The information processing apparatus of feature (13), in which the sensor includes a biological sensor that detects a biological signal of the user, and the biological signal is wirelessly sent from the communication section after the synchronizing signal has been assigned to the biological signal detected by the biological sensor.

(15)

The information processing apparatus of feature (13) or (14) further including:

a host device adapted to receive the captured image data from each of the information processing apparatus and the other information processing apparatus, in which the host device estimates a sticking position of each of the information processing apparatus and the other information processing apparatus on the basis of the captured image data received and performs image correction to ensure that a viewing angle and a center position of one piece of the captured image data match those of the other piece of the captured image data.

(16)

The information processing apparatus of feature (15), in which the sensor includes a myoelectric potential sensor that detects a myoelectric potential around the user's eyeball, and the host device detects a gazing point of the user on the basis of myoelectric potential data received from the information processing apparatus and the other information processing apparatus.

(16-1)

The information processing apparatus of feature (16), in which the host device further includes a recording section that records video data received from the information processing apparatus and the other information processing apparatus in association with the user's gazing point.

(16-2)

The information processing apparatus of feature (16), in which the information processing apparatus estimates an emotion of the user on the basis of the myoelectric potential data.

(16-3)

The information processing apparatus of feature (16), in which the information processing apparatus and the other information processing apparatus each further include an orbicularis oculi muscle sensor that detects orbicularis oculi muscles of the user, and the host device sends orbicularis oculi muscle data, received from the information processing apparatus and the other information processing apparatus, to a stickable device having an orbicularis oculi muscle actuator stuck near an eyeball of another user.

(17)

The information processing apparatus of any one of features (1) to (16), in which the sensor includes an odor sensor, the information processing apparatus further including:

an odor suppression section having at least one of a fragrancing function or a deodorizing function, in which the control section controls fragrancing or deodorizing by the odor suppression section on the basis of odor data detected by the odor sensor.

(18)

The information processing apparatus of any one of features (1) to (17), in which the control section controls fragrancing or deodorizing by the odor suppression section on the basis of context of the user and on the basis of odor data detected by the odor sensor.

(18-1)

The information processing apparatus of any one of features (1) to (18) further including:

a temperature control section capable of controlling the temperature, in which the control section controls the body temperature control section on the basis of sensor data detected by the sensor or the user's context.

(19)

A control method of an information processing apparatus, the information processing apparatus including a sensor, a communication section adapted to wirelessly communicate with external equipment, a control section adapted to control the sensor and the communication section, a power supply section adapted to supply power to at least one of the sensor, the communication section, or the control section, a housing section adapted to accommodate at least one of the sensor, the communication section, the control section, or the power supply section, a sticking section adapted to fasten the housing section to a user, and a sticking sensor adapted to detect a state of sticking between the user and the housing on the sticking section, the control method including:

a step of acquiring detection results of the sticking sensor;

a step of determining whether the sticking section has peeled off from the user or is just about to peel off from the user on the basis of the detection results; and a step of wirelessly sending a given signal to external equipment via the communication section when the sticking section has peeled off from the user or is just about to peel off from the user.

(20)

A recording medium recording a computer program for controlling an information processing apparatus, the information processing apparatus including a sensor, a communication section adapted to wirelessly communicate with external equipment, a control section adapted to control the sensor and the communication section, a power supply section adapted to supply power to at least one of the sensor, the communication section, or the control section, a housing section adapted to accommodate at least one of the sensor, the communication section, the control section, or the power supply section, a sticking section adapted to fasten the housing section to a user, and a sticking sensor adapted to detect a state of sticking between the user and the housing on the sticking section, the computer program written in a computer-readable form to cause a computer to perform:

a step of acquiring detection results of the sticking sensor;

a step of determining whether the sticking section has peeled off from the user or is just about to peel off from the user on the basis of the detection results; and a step of wirelessly sending a given signal to external equipment via the communication section when the sticking section has peeled off from the user or is just about to peel off from the user.

REFERENCE SIGNS LIST

100 . . . Stickable device
101 . . . Electric section,
102 . . . Housing section
103 . . . Sticking section,
104 . . . Body fluid treatment section
500 . . . Substrate,
501 . . . Sound pickup sensor,
502 . . . Control section
503 . . . Chip antenna,
504 . . . Power supply section
710 . . . Sensor section
711 . . . First sensor section,
712 . . . Second sensor section
720 . . . Actuator section
721 . . . First actuator section,
722 . . . Second actuator section
730 . . . Communication section
1400 . . . Stickable device,
1401 . . . Imaging section,
1402 . . . Exposure control section
1403 . . . Myoelectric potential measurement section,
1404 . . . Wireless communication section, 1405 . . . Synchronization section
1406 . . . Sticking sensor,
1407 . . . Control section,
1408 . . . Power supply section
1409 . . . Orbicularis oculi muscle sensor
1410 . . . Host device,
1411, 1412 . . . Wireless communication section
1413 . . . Sticking position estimation section,
1414 . . . Eyeball position estimation section
1415 . . . Command/gesture recognition section,
1416 . . . Communication section
1500 . . . Remote device,
1501 . . . Reception section,
1502 . . . Display section
1600 . . . Stickable device (for remote user)
1601 . . . Wireless communication section,
1602 . . . Orbicularis oculi muscle actuator
1700 . . . Stickable device
1710 . . . Sticking section,
1720 . . . Main body section,
1721 . . . Sticking sensor
1722 . . . Power supply section,
1723 . . . Control section,
1724 . . . Biological sensor
1725 . . . Odor sensor,
1726 . . . Body temperature control section,
1727 . . . Deodorizing section
1728 . . . Fragrancing section,
1729 . . . Wireless communication section
1750 . . . Host device,
1751 . . . Wireless communication section
1752 . . . Activity management section,
1753 . . . Environmental measurement section,
1754 . . . Control section

The invention claimed is:

1. A first information processing apparatus, comprising:
a sensor configured to detect sensor data;
a communication section configured to wirelessly communicate with an external equipment;
a control section configured to control the sensor and the communication section;
a power supply section configured to supply power to at least one of the sensor, the communication section, or the control section;
a housing section configured to accommodate at least one of the sensor, the communication section, the control section, or the power supply section;
a sticking section configured to fasten the housing section to a user, wherein
a surface of the sticking section is protected with release paper before use of the first information processing apparatus, and
the first information processing apparatus is activated based on peel-off of the release paper from the sticking section; and
a sticking sensor configured to detect a state of sticking between the user and the housing on the sticking section, wherein the control section is further configured to control communication operation of the communication section based on the detection of the state of sticking between the user and the housing.

2. The first information processing apparatus of claim 1, wherein the control section is further configured to control wireless transmission of a first signal to the external equipment via the communication section based on the detection, by the sticking sensor, that the sticking section has peeled off from the user or is just about to peel off from the user.

3. The first information processing apparatus of claim 2, further comprising:
a host device configured to engage in wireless communication via the communication section.

4. The first information processing apparatus of claim 3, wherein the host device is further configured to notify the user based on reception of a second signal.

5. The first information processing apparatus of claim 4, wherein the host device is further configured to:
execute an authentication procedure of the user based on the sensor data detected by the sensor, and
control cancellation of a user authentication established by the authentication procedure based on the reception of the second signal.

6. The first information processing apparatus of claim 1, further comprising:
a storage section configured to store internal information of the first information processing apparatus, wherein the control section is further configured to initialize or delete specific information stored in the storage section based on the detection, by the sticking sensor, that the sticking section has peeled off from the user or is just about to peel off from the user.

7. The first information processing apparatus of claim 6, wherein
the storage section is further configured to store equipment information of the first information processing apparatus, and
the control section is further configured to initialize or delete the equipment information stored in the storage section based on the detection, by the sticking sensor, that the sticking section has peeled off from the user or is just about to peel off from the user.

8. The first information processing apparatus of claim 6, wherein
the storage section is further configured to store the sensor data detected by the sensor, and
the control section is further configured to initialize or delete the sensor data stored in the storage section based on the detection, by the sticking sensor, that the sticking section has peeled off from the user or is just about to peel off from the user.

9. The first information processing apparatus of claim 1, wherein
the release paper includes a non-conductive section in a shape of a tongue piece that insulates the power supply section, and
based on peel-off of the release paper from the sticking section, the non-conductive section is detached to bring the power supply section into a conductive state.

10. The first information processing apparatus of claim 1, wherein the control section is further configured to activate the first information processing apparatus based on the detection, by the sticking sensor, that the release paper has been peeled off from the sticking section.

11. The first information processing apparatus of claim 1, wherein
the sensor includes an imaging sensor having an imaging function, and
the housing section is stuck near at least one of a user's first eyeball or a user's second eyeball to capture an image that corresponds to at least part of a user's field of view by the imaging sensor.

12. The first information processing apparatus of claim 11, wherein
the housing section is stuck near the user's first eyeball, and a synchronizing signal is stuck near the user's second eyeball, wherein
the synchronizing signal is assigned to wirelessly send captured image data captured by the imaging sensor from the communication section, and
the synchronizing signal is shared with a second information processing apparatus.

13. The first information processing apparatus of claim 12, wherein
the sensor includes a biological sensor configured to detect a biological signal of the user, and
the biological signal is wirelessly sent from the communication section after the synchronizing signal is assigned to the biological signal detected by the biological sensor.

14. The first information processing apparatus of claim 12, further comprising:
a host device configured to:
receive the captured image data from each of the first information processing apparatus and the second information processing apparatus;
estimate a sticking position of each of the first information processing apparatus and the second information processing apparatus based on the received captured image data; and
execute image correction to correct a viewing angle and a center position of a first piece of the captured image data match those of a second piece of the captured image data.

15. The first information processing apparatus of claim 14, wherein
the sensor further includes a myoelectric potential sensor configured to detect a myoelectric potential around the user's first eyeball and the user's second eyeball, and
the host device is further configured to detect a gazing point of the user based on myoelectric potential data received from the first information processing apparatus and the second information processing apparatus.

16. The first information processing apparatus of claim 1, wherein
the sensor includes an odor sensor, and
the first information processing apparatus further comprising:
an odor suppression section having at least one of a fragrancing function or a deodorizing function, and
the control section is further configured to control the fragrancing function or deodorizing function based on odor data detected by the odor sensor.

17. The first information processing apparatus of claim 1, wherein
the sensor includes an odor sensor, and
the first information processing apparatus further comprising:
an odor suppression section having at least one of a fragrancing function or a deodorizing function; and
the control section is further configured to control the fragrancing function or deodorizing function based on context of the user and odor data detected by the odor sensor.

18. A control method of an information processing apparatus, the information processing apparatus including:
a sensor,
a communication section configured to wirelessly communicate with an external equipment,
a control section configured to control the sensor and the communication section,
a power supply section configured to supply power to at least one of the sensor, the communication section, or the control section,
a housing section configured to accommodate at least one of the sensor, the communication section, the control section, or the power supply section,
a sticking section configured to fasten the housing section to a user, wherein
a surface of the sticking section is protected with release paper before use of the information processing apparatus, and
the information processing apparatus is activated based on peel-off of the release paper from the sticking section, and
a sticking sensor configured to detect a state of sticking between the user and the housing on the sticking section, the control method comprising:
acquiring detection results of the sticking sensor;
determining whether the sticking section has peeled off from the user or is just about to peel off from the user based on the detection results; and
transmitting a specific signal wirelessly to an external equipment via the communication section based on a determination that the sticking section has peeled off from the user or is just about to peel off from the user.

19. A non-transitory computer-readable medium having stored thereon computer-executable instructions that, when executed by a processor, cause the processor to execute operations, by an information processing apparatus that includes:
a sensor,
a communication section configured to wirelessly communicate with an external equipment,
a control section configured to control the sensor and the communication section,
a power supply section configured to supply power to at least one of the sensor, the communication section, or the control section,
a housing section configured to accommodate at least one of the sensor, the communication section, the control section, or the power supply section,
a sticking section configured to fasten the housing section to a user, wherein
a surface of the sticking section is protected with release paper before use of the information processing apparatus, and
the information processing apparatus is activated based on peel-off of the release paper from the sticking section; and
a sticking sensor configured to detect a state of sticking between the user and the housing on the sticking section, and
the operations comprising:
acquiring detection results of the sticking sensor;
determining whether the sticking section has peeled off from the user or is just about to peel off from the user based on the detection results; and
transmitting a given signal wirelessly to an external equipment via the communication section based on a determination that the sticking section has peeled off from the user or is just about to peel off from the user.

* * * * *